US012801888B2

(12) United States Patent
Zamir et al.

(10) Patent No.: US 12,801,888 B2
(45) Date of Patent: Nov. 17, 2026

(54) PRE-ENCODING METHOD FOR DNA STORAGE

(71) Applicant: Western Digital Technologies, Inc., San Jose, CA (US)

(72) Inventors: Ran Zamir, Ramat Gan (IL); Alexander Bazarsky, Holon (IL); David Avraham, Even Yehuda (IL)

(73) Assignee: WESTERN DIGITAL TECHNOLOGIES, INC., San Jose, CA (US)

( * ) Notice: Subject to any disclaimer, the term of this patent is extended or adjusted under 35 U.S.C. 154(b) by 468 days.

(21) Appl. No.: 18/355,206

(22) Filed: Jul. 19, 2023

(65) Prior Publication Data

US 2024/0185021 A1 Jun. 6, 2024

Related U.S. Application Data

(60) Provisional application No. 63/429,208, filed on Dec. 1, 2022.

(51) Int. Cl.
*G06N 3/00* (2023.01)
*G16B 50/30* (2019.01)
*G16B 50/40* (2019.01)

(52) U.S. Cl.
CPC ............. *G06N 3/002* (2013.01); *G16B 50/30* (2019.02); *G16B 50/40* (2019.02)

(58) Field of Classification Search
CPC ........ G06N 3/002; G16B 50/30; G16B 50/40; G16B 50/50
See application file for complete search history.

(56) References Cited

U.S. PATENT DOCUMENTS 7,809,142 B2 * 10/2010 Bohush ..................... H04L 9/16 713/193
9,483,656 B2 * 11/2016 Leggette ............. G06F 11/1076
(Continued)

OTHER PUBLICATIONS

Fei, Peng, et al., "LDPC Codes for Portable DNA Storage", 2019 IEEE International Symposium on Information Theory (ISIT), Jul. 2019, pp. 76-80, https://doi.org/10.1109/ISIT.2019.8849814.
(Continued)

*Primary Examiner* — Lam T Mai
(74) *Attorney, Agent, or Firm* — Dentons Durham Jones Pinegar P.C.

(57) ABSTRACT

A computer-implemented method includes receiving an encoding table defining a plurality of mappings between input segments and encoded segments, where each encoded segment defines an ordered string of data representing a sequence of one or more deoxyribonucleic acid (DNA) nucleotide bases; identifying an input string of input data; segmenting the input string into a plurality of input tuples; for each input tuple, generate a plurality of encoded tuples by identifying an entry of the encoding table that has an input segment equal to the input tuple and adding an encoded tuple that includes an encoded segment; converting the plurality of encoded tuples into a DNA sequence string of DNA nucleotides by concatenating the plurality of encoded tuples in an order defined by the plurality of input tuples; and transmitting the DNA sequence string of DNA nucleotides to be used for synthesizing at least one DNA molecule.

20 Claims, 10 Drawing Sheets

(56) References Cited

U.S. PATENT DOCUMENTS

| | | | | |
|---|---|---|---|---|
| 10,020,826 | B2 | 7/2018 | Gladwin et al. | |
| 10,090,857 | B2 * | 10/2018 | Bhola | G16B 50/50 |
| 10,963,469 | B2 | 3/2021 | Taig et al. | |
| 11,100,404 | B2 * | 8/2021 | Merriman | G16B 30/20 |
| 2008/0317242 | A1 * | 12/2008 | Bohush | H04L 9/16 380/28 |
| 2012/0089652 | A1 * | 4/2012 | Ganeshalingam | G16B 30/10 707/825 |
| 2013/0346830 | A1 * | 12/2013 | Ordentlich | G06F 11/1048 714/767 |
| 2015/0248430 | A1 * | 9/2015 | Hospodor | G16C 99/00 707/700 |
| 2015/0339341 | A1 * | 11/2015 | Moore | G06F 16/2237 707/693 |
| 2017/0357749 | A1 * | 12/2017 | Laine | G16B 50/40 |
| 2018/0232525 | A1 * | 8/2018 | Calahan | G06F 16/22 |
| 2019/0317684 | A1 * | 10/2019 | Kwon | H03M 7/30 |
| 2020/0321079 | A1 | 10/2020 | Huang et al. | |
| 2021/0050864 | A1 * | 2/2021 | Breslow | G06F 3/0661 |
| 2021/0398618 | A1 * | 12/2021 | Ma | G16B 30/10 |
| 2022/0042070 | A1 | 2/2022 | Eppler et al. | |
| 2022/0237470 | A1 | 7/2022 | Vishwakarma et al. | |
| 2023/0317300 | A1 * | 10/2023 | Noto | G16H 70/60 705/2 |
| 2024/0168676 | A1 * | 5/2024 | Avraham | G16B 30/00 |
| 2024/0176733 | A1 * | 5/2024 | Avraham | G06N 3/123 |
| 2024/0193037 | A1 * | 6/2024 | Avraham | G16B 30/10 |
| 2024/0426778 | A1 * | 12/2024 | Kinney | G01N 27/44786 |
| 2025/0137990 | A1 * | 5/2025 | Kinney | G01N 33/48721 |
| 2025/0137991 | A1 * | 5/2025 | Kinney | G01N 33/48721 |
| 2025/0174272 | A1 * | 5/2025 | Zamir | G16B 50/30 |
| 2025/0183915 | A1 * | 6/2025 | Bazarsky | G06N 3/123 |
| 2025/0191696 | A1 * | 6/2025 | Avraham | G06F 11/008 |

OTHER PUBLICATIONS

Ross et al., "Characterizing and measuring bias in sequence data", Genome Biology 2013, 14:R51, http://genomebiology.com/2013/14/5/R51.

* cited by examiner

300

ENCODING TABLE 310 312 314 316

320

| # | BASE-2 | BASE-4 | *k*-BIT |
|---|---|---|---|
| 0 | 00000000 | AAAA | REP |
| 1 | 00000001 | AAAT | REP |
| 2 | 00000010 | AAAG | REP |
| 3 | 00000011 | AAAC | REP |
| 4 | 00000100 | AATA | REP |
| 5 | 00000101 | AATT | REP |
| 6 | 00000110 | AATG | REP |
| 7 | 00000111 | AATC | REP |
| 8 | 00001000 | AAGA | REP |
| 9 | 00001001 | AAGT | REP |
| 10 | 00001010 | AAGG | REP |
| 11 | 00001011 | AAGC | REP |
| 12 | 00001100 | AACA | REP |
| 13 | 00001101 | AACT | REP |
| 14 | 00001110 | AACG | REP |
| 15 | 00001111 | AACC | REP |
| 16 | 00010000 | ATAA | REP |
| 17 | 00010001 | ATAT | T |
| 18 | 00010010 | ATAG | T |
| 19 | 00010011 | ATAC | T |
| 20 | 00010100 | ATTA | REP |
| 21 | 00010101 | ATTT | REP |
| 22 | 00010110 | ATTG | REP |
| 23 | 00010111 | ATTC | REP |
| 24 | 00011000 | ATGA | T |
| 25 | 00011001 | ATGT | T |
| 26 | 00011010 | ATGG | REP |
| 27 | 00011011 | ATGC | T |
| 28 | 00011100 | ATCA | T |
| 29 | 00011101 | ATCT | T |
| 30 | 00011110 | ATCG | T |
| 31 | 00011111 | ATCC | REP |

ENCODING TABLE (CONT.)

| # | BASE-2 | BASE-4 | *k*-BIT |
|---|---|---|---|
| 32 | 00100000 | AGAA | REP |
| 33 | 00100001 | AGAT | 000000 |
| 34 | 00100010 | AGAG | 000001 |
| 35 | 00100011 | AGAC | 000010 |
| 36 | 00100100 | AGTA | 000011 |
| 37 | 00100101 | AGTT | REP |
| 38 | 00100110 | AGTG | 000100 |
| 39 | 00100111 | AGTC | 000101 |
| 40 | 00101000 | AGGA | REP |
| 41 | 00101001 | AGGT | REP |
| 42 | 00101010 | AGGG | REP |
| 43 | 00101011 | AGGC | REP |
| 44 | 00101100 | AGCA | 000110 |
| 45 | 00101101 | AGCT | 000111 |
| 46 | 00101110 | AGCG | 001000 |
| 47 | 00101111 | AGCC | REP |
| 48 | 00110000 | ACAA | REP |
| 49 | 00110001 | ACAT | 001001 |
| 50 | 00110010 | ACAG | 001010 |
| 51 | 00110011 | ACAC | 001011 |
| 52 | 00110100 | ACTA | 001100 |
| 53 | 00110101 | ACTT | REP |
| 54 | 00110110 | ACTG | 001101 |
| 55 | 00110111 | ACTC | 001110 |
| 56 | 00111000 | ACGA | 001111 |
| 57 | 00111001 | ACGT | 010000 |
| 58 | 00111010 | ACGG | REP |
| 59 | 00111011 | ACGC | 010001 |
| 60 | 00111100 | ACCA | REP |
| 61 | 00111101 | ACCT | REP |
| 62 | 00111110 | ACCG | REP |
| 63 | 00111111 | ACCC | REP |

FIG. 3A

300

ENCODING TABLE (CONT.)

310 312 314 316

320

| # | BASE-2 | BASE-4 | *k*-BIT |
|---|---|---|---|
| 64 | 01000000 | TAAA | REP |
| 65 | 01000001 | TAAT | REP |
| 66 | 01000010 | TAAG | REP |
| 67 | 01000011 | TAAC | REP |
| 68 | 01000100 | TATA | T |
| 69 | 01000101 | TATT | REP |
| 70 | 01000110 | TATG | T |
| 71 | 01000111 | TATC | T |
| 72 | 01001000 | TAGA | T |
| 73 | 01001001 | TAGT | T |
| 74 | 01001010 | TAGG | REP |
| 75 | 01001011 | TAGC | T |
| 76 | 01001100 | TACA | T |
| 77 | 01001101 | TACT | T |
| 78 | 01001110 | TACG | T |
| 79 | 01001111 | TACC | REP |
| 80 | 01010000 | TTAA | REP |
| 81 | 01010001 | TTAT | REP |
| 82 | 01010010 | TTAG | REP |
| 83 | 01010011 | TTAC | REP |
| 84 | 01010100 | TTTA | REP |
| 85 | 01010101 | TTTT | REP |
| 86 | 01010110 | TTTG | REP |
| 87 | 01010111 | TTTC | REP |
| 88 | 01011000 | TTGA | REP |
| 89 | 01011001 | TTGT | REP |
| 90 | 01011010 | TTGG | REP |
| 91 | 01011011 | TTGC | REP |
| 92 | 01011100 | TTCA | REP |
| 93 | 01011101 | TTCT | REP |
| 94 | 01011110 | TTCG | REP |
| 95 | 01011111 | TTCC | REP |

ENCODING TABLE (CONT.)

| # | BASE-2 | BASE-4 | *k*-BIT |
|---|---|---|---|
| 96 | 01100000 | TGAA | REP |
| 97 | 01100001 | TGAT | T |
| 98 | 01100010 | TGAG | T |
| 99 | 01100011 | TGAC | T |
| 100 | 01100100 | TGTA | T |
| 101 | 01100101 | TGTT | REP |
| 102 | 01100110 | TGTG | T |
| 103 | 01100111 | TGTC | T |
| 104 | 01101000 | TGGA | REP |
| 105 | 01101001 | TGGT | REP |
| 106 | 01101010 | TGGG | REP |
| 107 | 01101011 | TGGC | REP |
| 108 | 01101100 | TGCA | T |
| 109 | 01101101 | TGCT | T |
| 110 | 01101110 | TGCG | T |
| 111 | 01101111 | TGCC | REP |
| 112 | 01110000 | TCAA | REP |
| 113 | 01110001 | TCAT | T |
| 114 | 01110010 | TCAG | T |
| 115 | 01110011 | TCAC | T |
| 116 | 01110100 | TCTA | T |
| 117 | 01110101 | TCTT | REP |
| 118 | 01110110 | TCTG | T |
| 119 | 01110111 | TCTC | T |
| 120 | 01111000 | TCGA | T |
| 121 | 01111001 | TCGT | T |
| 122 | 01111010 | TCGG | REP |
| 123 | 01111011 | TCGC | T |
| 124 | 01111100 | TCCA | REP |
| 125 | 01111101 | TCCT | REP |
| 126 | 01111110 | TCCG | REP |
| 127 | 01111111 | TCCC | REP |

FIG. 3B

300

ENCODING TABLE (CONT.)

310 312 314 316

320 → (row 128)

| # | BASE-2 | BASE-4 | *k*-BIT |
|---|---|---|---|
| 128 | 10000000 | GAAA | REP |
| 129 | 10000001 | GAAT | REP |
| 130 | 10000010 | GAAG | REP |
| 131 | 10000011 | GAAC | REP |
| 132 | 10000100 | GATA | 010010 |
| 133 | 10000101 | GATT | REP |
| 134 | 10000110 | GATG | 010011 |
| 135 | 10000111 | GATC | 010100 |
| 136 | 10001000 | GAGA | 010101 |
| 137 | 10001001 | GAGT | 010110 |
| 138 | 10001010 | GAGG | REP |
| 139 | 10001011 | GAGC | 010111 |
| 140 | 10001100 | GACA | 011000 |
| 141 | 10001101 | GACT | 011001 |
| 142 | 10001110 | GACG | 011010 |
| 143 | 10001111 | GACC | REP |
| 144 | 10010000 | GTAA | REP |
| 145 | 10010001 | GTAT | T |
| 146 | 10010010 | GTAG | T |
| 147 | 10010011 | GTAC | T |
| 148 | 10010100 | GTTA | REP |
| 149 | 10010101 | GTTT | REP |
| 150 | 10010110 | GTTG | REP |
| 151 | 10010111 | GTTC | REP |
| 152 | 10011000 | GTGA | T |
| 153 | 10011001 | GTGT | T |
| 154 | 10011010 | GTGG | REP |
| 155 | 10011011 | GTGC | T |
| 156 | 10011100 | GTCA | T |
| 157 | 10011101 | GTCT | T |
| *** 158 | 10011110 | GTCG | 011011 |
| 159 | 10011111 | GTCC | REP |

ENCODING TABLE (CONT.)

| # | BASE-2 | BASE-4 | *k*-BIT |
|---|---|---|---|
| 160 | 10100000 | GGAA | REP |
| 161 | 10100001 | GGAT | REP |
| 162 | 10100010 | GGAG | REP |
| 163 | 10100011 | GGAC | REP |
| 164 | 10100100 | GGTA | REP |
| 165 | 10100101 | GGTT | REP |
| 166 | 10100110 | GGTG | REP |
| 167 | 10100111 | GGTC | REP |
| 168 | 10101000 | GGGA | REP |
| 169 | 10101001 | GGGT | REP |
| 170 | 10101010 | GGGG | REP |
| 171 | 10101011 | GGGC | REP |
| 172 | 10101100 | GGCA | REP |
| 173 | 10101101 | GGCT | REP |
| 174 | 10101110 | GGCG | REP |
| 175 | 10101111 | GGCC | REP |
| 176 | 10110000 | GCAA | REP |
| 177 | 10110001 | GCAT | 011100 |
| 178 | 10110010 | GCAG | 011101 |
| 179 | 10110011 | GCAC | 011110 |
| 180 | 10110100 | GCTA | 011111 |
| 181 | 10110101 | GCTT | REP |
| 182 | 10110110 | GCTG | 100000 |
| 183 | 10110111 | GCTC | 100001 |
| 184 | 10111000 | GCGA | 100010 |
| 185 | 10111001 | GCGT | 100011 |
| 186 | 10111010 | GCGG | REP |
| 187 | 10111011 | GCGC | 100100 |
| 188 | 10111100 | GCCA | REP |
| 189 | 10111101 | GCCT | REP |
| 190 | 10111110 | GCCG | REP |
| 191 | 10111111 | GCCC | REP |

FIG. 3C

300

ENCODING TABLE (CONT.)

310 312 314 316

320

| # | BASE-2 | BASE-4 | k-BIT |
|---|---|---|---|
| 192 | 11000000 | CAAA | REP |
| 193 | 11000001 | CAAT | REP |
| 194 | 11000010 | CAAG | REP |
| 195 | 11000011 | CAAC | REP |
| 196 | 11000100 | CATA | 100101 |
| 197 | 11000101 | CATT | REP |
| 198 | 11000110 | CATG | 100110 |
| 199 | 11000111 | CATC | 100111 |
| 200 | 11001000 | CAGA | 101000 |
| 201 | 11001001 | CAGT | 101001 |
| 202 | 11001010 | CAGG | REP |
| 203 | 11001011 | CAGC | 101010 |
| 204 | 11001100 | CACA | 101011 |
| 205 | 11001101 | CACT | 101100 |
| 206 | 11001110 | CACG | 101101 |
| 207 | 11001111 | CACC | REP |
| 208 | 11010000 | CTAA | REP |
| 209 | 11010001 | CTAT | 101110 |
| 210 | 11010010 | CTAG | 101111 |
| 211 | 11010011 | CTAC | 110000 |
| 212 | 11010100 | CTTA | REP |
| 213 | 11010101 | CTTT | REP |
| 214 | 11010110 | CTTG | REP |
| 215 | 11010111 | CTTC | REP |
| 216 | 11011000 | CTGA | 110001 |
| 217 | 11011001 | CTGT | 110010 |
| 218 | 11011010 | CTGG | REP |
| 219 | 11011011 | CTGC | 110011 |
| 220 | 11011100 | CTCA | 110100 |
| 221 | 11011101 | CTCT | 110101 |
| 222 | 11011110 | CTCG | 110110 |
| 223 | 11011111 | CTCC | REP |

ENCODING TABLE (CONT.)

| # | BASE-2 | BASE-4 | k-BIT |
|---|---|---|---|
| 224 | 11100000 | CGAA | REP |
| 225 | 11100001 | CGAT | 110111 |
| 226 | 11100010 | CGAG | 111000 |
| 227 | 11100011 | CGAC | 111001 |
| 228 | 11100100 | CGTA | 111010 |
| 229 | 11100101 | CGTT | REP |
| 230 | 11100110 | CGTG | 111011 |
| 231 | 11100111 | CGTC | 111100 |
| 232 | 11101000 | CGGA | REP |
| 233 | 11101001 | CGGT | REP |
| 234 | 11101010 | CGGG | REP |
| 235 | 11101011 | CGGC | REP |
| 236 | 11101100 | CGCA | 111101 |
| 237 | 11101101 | CGCT | 111110 |
| 238 | 11101110 | CGCG | 111111 |
| 239 | 11101111 | CGCC | REP |
| 240 | 11110000 | CCAA | REP |
| 241 | 11110001 | CCAT | REP |
| 242 | 11110010 | CCAG | REP |
| 243 | 11110011 | CCAC | REP |
| 244 | 11110100 | CCTA | REP |
| 245 | 11110101 | CCTT | REP |
| 246 | 11110110 | CCTG | REP |
| 247 | 11110111 | CCTC | REP |
| 248 | 11111000 | CCGA | REP |
| 249 | 11111001 | CCGT | REP |
| 250 | 11111010 | CCGG | REP |
| 251 | 11111011 | CCGC | REP |
| 252 | 11111100 | CCCA | REP |
| 253 | 11111101 | CCCT | REP |
| 254 | 11111110 | CCCG | REP |
| 255 | 11111111 | CCCC | REP |

FIG. 3D

PRE-ENCODING METHOD FOR DNA STORAGE

CROSS-REFERENCE TO RELATED APPLICATIONS

The present application claims priority to U.S. Provisional Application 63/429,208 entitled "PRE-ENCODING METHOD FOR DNA STORAGE", filed Dec. 1, 2022, the entire disclosure of which is hereby incorporated by reference in its entirety.

BACKGROUND

DNA-based storage systems are emerging as a promising storage technology. DNA is a long molecule made up of four nucleotide bases—adenine (A), cytosine (C), thymine (T) and guanine (G). For storage purposes, base units (ACTG) of synthesized DNA can be used to encode information—similar to how a string of ones and zeros represent data in traditional electronic storage systems. The encoded information may then be stored, subsequently accessed and decoded.

For example, DNA-based storage systems typically store DNA data using three main processes—synthesis (or writing) in which the base units of synthesized DNA are joined together to produce a desired DNA string; storage, in which the DNA string is stored in a DNA-based storage medium; and sequencing (or reading), in which the DNA string is translated to binary/digital data.

While DNA-based storage systems are more dense than traditional electronic data storage systems, DNA-based storage systems are more prone to errors. For example, during synthesis, storage and/or sequencing, various symbols in the DNA string may be inserted or deleted. In other examples, during synthesis, storage and/or sequencing, one symbol (or multiple symbols) in the DNA string may be substituted for another symbol.

Further, DNA-based storage systems may also be subject to errors based on the content of the data. For example, some current DNA storage systems and associated processes suffer from elevated error levels for homopolymer sequences (e.g., sequences with repetitions of the same base, such as "GGGG" or "CCCC"). Further, the T-base may exhibit more errors than the other bases in some systems, and the high content of base pairs of "GC" may also exhibit elevated error rates in certain processes. Accordingly, what is needed is a DNA storage system that can change, or "shape," the input data to avoid such error-prone situations.

SUMMARY

The present application describes a computing system. The computing system includes a memory device storing an encoding table. The encoding table defines a plurality of mappings between a plurality of input segments and a plurality of encoded segments. Each input segment of the plurality of input segments is associated in the encoding table with an encoded segment of the plurality of encoded segments. Each encoded segment defines a string of data representing a sequence of one or more deoxyribonucleic acid (DNA) nucleotide bases. The computing system also includes at least one processor executing instructions that are configured to cause the at least one processor to: (i) identify an input string of input data; (ii) segment the input string into a plurality of input tuples, each input tuple of the plurality of input tuples being k bits in size; (iii) for each input tuple of the plurality of input tuples, generate a plurality of encoded tuples by: (a) identifying an entry of the encoding table that has an input segment equal to the input tuple; and (b) adding, to the plurality of encoded tuples, an encoded tuple that includes an encoded segment in the identified entry of the encoding table; (iv) convert the plurality of encoded tuples into a DNA sequence string of DNA nucleotides by concatenating the plurality of encoded tuples in an order defined by the plurality of input tuples; and (v) cause at least one DNA molecule to be synthesized using the DNA sequence string of DNA nucleotides.

The present application also describes a computer-implemented method. The computer-implemented method includes receiving an encoding table. The encoding table defines a plurality of mappings between a plurality of input segments and a plurality of encoded segments. Each input segment of the plurality of input segments is associated in the encoding table with an encoded segment of the plurality of encoded segments. Each encoded segment defines a string of data representing a sequence of one or more deoxyribonucleic acid (DNA) nucleotide bases. The computer-implemented method also includes identifying an input string of input data. The computer-implemented method further includes segmenting the input string into a plurality of input tuples, each input tuple of the plurality of input tuples being k bits in size. The computer-implemented method also includes, for each input tuple of the plurality of input tuples, generate a plurality of encoded tuples by: (a) identifying an entry of the encoding table that has an input segment equal to the input tuple; and (b) adding, to the plurality of encoded tuples, an encoded tuple that includes an encoded segment in the identified entry of the encoding table. The computer-implemented method further includes converting the plurality of encoded tuples into a DNA sequence string of DNA nucleotides by concatenating the plurality of encoded tuples in an order defined by the plurality of input tuples. The computer-implemented method also includes transmitting the DNA sequence string of DNA nucleotides to be used for synthesizing at least one DNA molecule.

The present application further describes a non-transitory, computer-readable storage medium comprising instructions. When executed by at least one processor, the instructions cause the at least one processor to identify an encoding table. The encoding table defines a plurality of mappings between a plurality of input segments and a plurality of encoded segments. Each input segment of the plurality of input segments being associated in the encoding table with an encoded segment of the plurality of encoded segments. Each encoded segment defines a string of data representing a sequence of one or more deoxyribonucleic acid (DNA) nucleotide bases. The instructions also cause the at least one processor to identify an input string of input data. The instructions further cause the at least one processor to perform means for segmenting the input string into a plurality of input tuples, each input tuple of the plurality of input tuples being k bits in size. The instructions also cause the at least one processor to, for each input tuple of the plurality of input tuples, generate a plurality of encoded tuples by: (a) means for identifying an entry of the encoding table that has an input segment equal to the input tuple; and (b) means for adding, to the plurality of encoded tuples, an encoded tuple that includes an encoded segment in the identified entry of the encoding table. The instructions further cause the at least one processor to perform means for converting the plurality of encoded tuples into a DNA sequence string of DNA nucleotides by concatenating the plurality of encoded tuples in an order defined by the plurality of input tuples. The instructions also cause the at least one processor to transmit the DNA sequence string of DNA nucleotides to be used for synthesizing at least one DNA molecule.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting and non-exhaustive examples are described with reference to the following Figures.

FIG. 3A to FIG. 3D illustrate an example encoding table that may be used by the DNA storage system of FIG. 2

DETAILED DESCRIPTION

Figure 1:
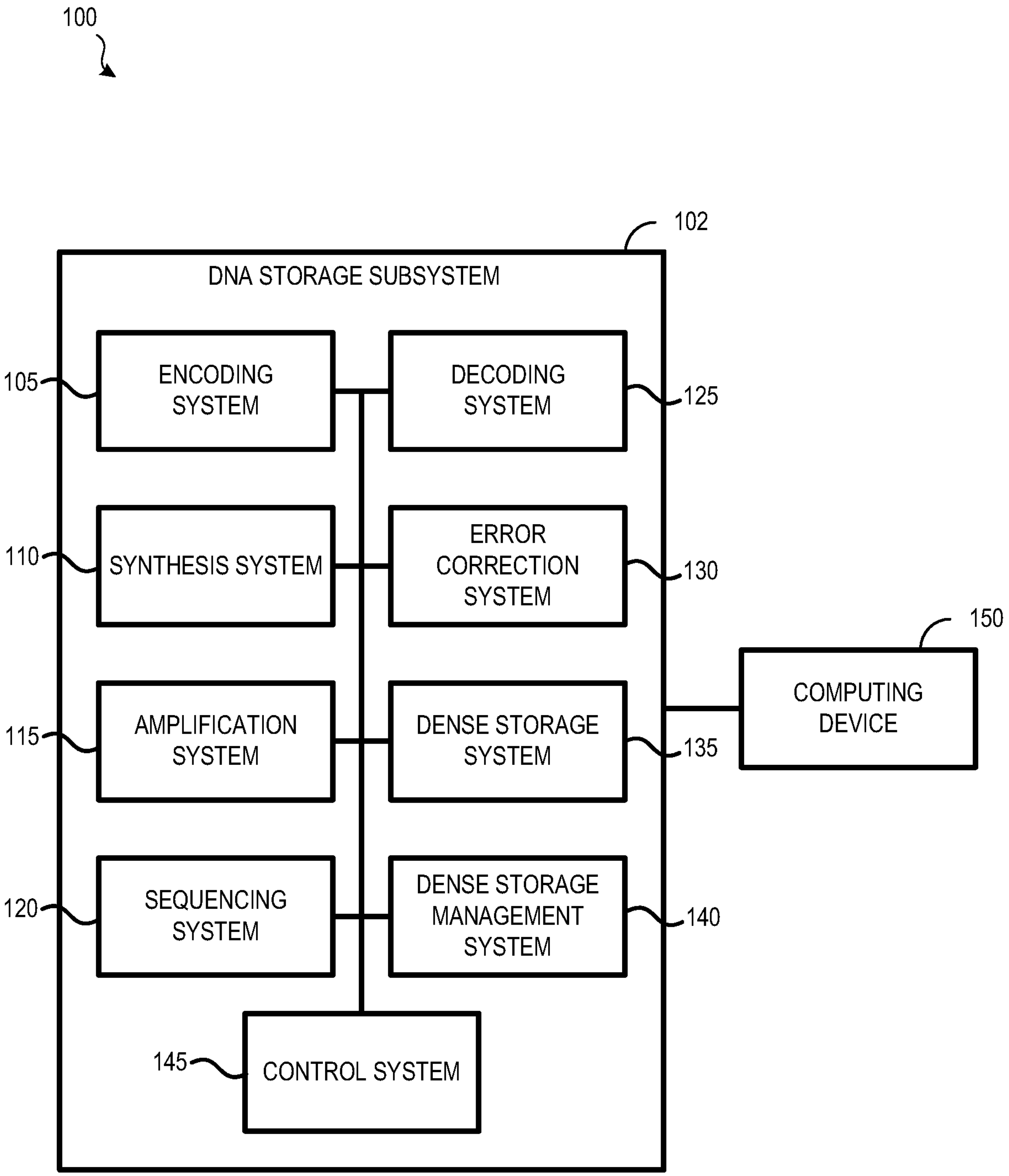
FIG. 1 illustrates a data storage system according to an example.

In the following detailed description, references are made to the accompanying drawings that form a part hereof, and in which are shown by way of illustrations specific embodiments or examples. These aspects may be combined, other aspects may be utilized, and structural changes may be made without departing from the present disclosure. Examples may be practiced as methods, systems or devices. Accordingly, examples may take the form of a hardware implementation, an entirely software implementation, or an implementation combining software and hardware aspects. The following detailed description is therefore not to be taken in a limiting sense, and the scope of the present disclosure is defined by the appended claims and their equivalents.

The DNA channel of conventional DNA storage systems can be subject to many types of errors. Some such errors can be introduced based on the content of the input data itself. For example, in some systems, the occurrence of homopolymer sequences (e.g., sequences with repetitions of the same base, such as "GGGG" or "CCCC") can yield more errors, the T-base can exhibit more errors than the other bases in some systems, and the high content of base pairs of "GC" may also exhibit elevated error rates in certain processes. As such, if left in its original form, the input data may exhibit many instances of such error-prone situations.

The present disclosure describes a DNA storage system and methods for improving DNA storage and, particularly, for providing an encoding process (e.g., prior to synthesis) that yields more accurate reconstitution of input data from DNA molecules (e.g., after sequencing and decoding). More specifically, in an example, the DNA storage system includes an encoding component that is configured to alter ("shape") the input data before synthesis. This shaping of the input data involves altering the input data to avoid DNA segments that have unwanted properties (e.g., that tend to exhibit greater errors). This alteration is performed using an encoding table that contains a list of all possible input segments of a given size (e.g., 6-bit segments) and a corresponding mapping to a particular encoded DNA segment (e.g., a particular segment of base pairs) for each possible input segment.

In an example, the encoding table is constructed with such mappings to avoid one or more types of error-prone data. In other words, an input segment that would otherwise be subject to greater errors through the synthesis and sequencing processes of the DNA data channel (e.g., the bit segment 010101, which may translate to "TTT" in DNA base pair encoding) may instead be mapped to a DNA segment that does not exhibit any of the identified error-prone situations (e.g., an encoded segment of "GAGA", which avoids both the contiguous base repetitions issue and the T-base issue). As such, each possible input bit segment of the input data (e.g., having $2^k$ unique variants, where k is the number of bits in the input bit segment) is assigned a mapping to an encoded segment that helps avoid the error-prone situations.

Since some or many DNA segments in the $2^k$ possible variants may be subject to higher errors, a larger mapping space is used for the encoded strings. For example, when using 6-bit input segments (e.g., 3 bases in DNA form), which have $2^6$ possible variants, the encoding table may map this input segment space to an 8-bit encoded space (e.g., $2^8$ possible variants, or 4 bases in DNA form). As such, out of the $2^8$ possible variants of the encoded space, the encoding table excludes any of the encoded segments that manifest the error-prone situations, and instead maps all $2^6$ input segments to only segments in the $2^8$ encoded space that do not exhibit the error-prone situations.

Accordingly, during encoding, the encoding system segments the input data into input segments of fixed size (e.g., 6-bit segments), converts each of those input segments into their corresponding encoded segment (e.g., based on the encoding table), then assembles a DNA string out of each of those encoded segments (e.g., concatenating the encoded segments in the same order as their associated input segments). The DNA storage system then uses that DNA string to synthesize DNA molecule(s) for long term storage. Similarly, after sequencing the DNA molecule(s), the resulting output sequence string is then decoded using the same encoding table and associated mappings. In the case of decoding, the sequence string is segmented into fixed-size segments (e.g., 8 bits, or 4 bases per segment), each of which is then reverse-mapped from the encoded segment space to the associated input segment space (e.g., from a 4-base encoded segment to a 3-base or 6-bit output segment). Once each of the encoded segments are decoded to their associated output segment, the output segments are then assembled to generate output data (e.g., an output string near or identical to the original input data).

Given that the encoded space is larger than the input space (e.g., $2^8>2^6$, which corresponds to 4 bases per segment instead of 3 bases per segment), the DNA storage system thus generates a longer DNA sequence for any given input data, but in exchange for improved results when sequencing the DNA molecule (e.g., since the encoded segments avoid some error-prone situations). As such, the DNA storage system and methods provide improvements in the accuracy and error rate when reconstituting input data from DNA molecules. Further, if the error level is improved via the encoding methods described herein, it may allow the DNA channel to use less error correction data (e.g., parity data, error correction codes, or the like), and thus may reduce computational complexity in correcting the sequenced data and use more of the channel for user data.

These various benefits and examples will be described in greater detail below with reference to FIG. 1-FIG. 6.

FIG. 1 illustrates a data storage system 100 according to an example. The data storage system 100 may be used to store data that is "more dense" when compared to data that is stored in a traditional electronic storage medium such as, for example, hard disks, optical disks, flash memory, and the like. For example, the data storage system 100 may be used to store synthetic DNA-based data.

DNA includes four naturally occurring nucleotide bases: adenine (A), cytosine (C), thymine (T) and guanine (G). In order to store data in synthetic DNA, received data is encoded to the various nucleotide bases. For example, data received as ones and zeros is encoded or otherwise mapped to various sequences of the synthetic DNA nucleotide bases. Once encoded, the data may be synthesized (e.g., written) and stored (e.g., in a dense storage system). To retrieve the stored data, the synthetic DNA molecules are sequenced (e.g., read) and subsequently decoded. As part of the decoding process, the synthetic DNA nucleotide bases are remapped to the original ones and zeros. Each of these processes will be discussed in greater detail below. Effectively, the binary system of 0's and 1's (e.g., two states of a binary "base-2" numeral system, represented in one conventional binary bit) are represented in a quaternary system of A's, C's, T's, and G's (e.g., four states of a quaternary "base-4" numeral system, represented by a single nucleotide of DNA) when the source binary (e.g., base-2) data is encoded in the quaternary (e.g., base-4) system of nucleotides.

Although synthetic DNA-based data and associated DNA-based storage systems are specifically mentioned, the systems and methods described herein may be applicable to traditional electronic storage mediums/systems and/or traditional digital/binary data.

In an example, the data storage system 100 includes an encoding system 105. The encoding system 105 receives digital/binary information and/or data (e.g., binary ones and zeros, or "base-2") from a computing device (e.g., computing device 150) or from another source. This data may be referred to herein as "input data," "source data," or "original data." Such input is initially stored and represented in conventional base-2 binary (e.g., when not embodied in DNA). When the input data is received, the encoding system 105 converts or maps the ones and zeros of the original data into various DNA sequences using the synthetic DNA nucleotide bases A, C, T, and G. For example, the DNA nucleotide base "A" may be assigned a value 00, the DNA nucleotide base "C" may be assigned a value 01 (base-2), the DNA nucleotide base "T" may be assigned a value 10 and the DNA nucleotide base "G" may be assigned a value 11. These binary-to-quaternary mappings, and their complements, are used in the examples provided herein, but it should be understood that any similar mapping may be used.

In one example, the encoding system 105 performs a "direct encoding" process when preparing input data for memorialization in DNA. Direct encoding includes the binary-to-quaternary mappings to translate or convert each pair of bits into a single nucleotide. For example, input data of 010010110100 may be directly encoded as a DNA sequence or DNA string of CATGCA. This data, when embodied in DNA form, may be referred to herein as "DNA data." Such direct encoding of data yields one nucleotide of DNA data for every two bits of input data. Other more complex encoding processes are described herein.

The data storage system 100 may also include a synthesis system 110. In an example, the synthesis system 110 writes or otherwise manufactures DNA strands based on the data provided by the encoding system 105. For example, using a series of chemical steps or processes, the synthesis system 110 creates and assembles the various DNA bases (e.g., the ACTG bases) are assembled to mirror the base-4 representation determined from the encoding process. Although chemical steps or processes are mentioned, the synthesis system 110 may use other synthesis techniques, and the synthesis system 110 includes both hardware components configured to create such DNA strings as well as software and/or electronic components for controlling those hardware components.

Continuing with the example above, during synthesis, since the digital data of 010010110100 is represented as CATGCA, the synthesis system 110 would first generate and/or identify a "C" base. An "A" base would then be generated and/or identified and be attached to the "C" base. A "T" base would then be generated and/or identified and be attached to the "CA" combination that was previously generated. This process repeats until the entire DNA string (e.g., CATGCA) is created. The terms "created", "generated", or "synthesized", and their variants, may be used interchangeably herein when referring to the making of an real-world synthetic string of DNA. Further, the terms "DNA string" and "DNA sequence" may also be used interchangeably to refer to the synthetic DNA molecule created during the processes described herein, or to a mathematical representation of that DNA string, depending on context.

When the synthesis process is complete, the DNA sequence is stored in a physical storage medium such as, for example, a dense storage system 135 (e.g., one or more synthetic DNA molecules). The dense storage system 135 enables the synthesized DNA sequence to be stored and subsequently accessed. In an example, any storage medium capable of storing DNA-based data may be used as the dense storage system 135.

Once the DNA sequence has been stored, it may be subsequently accessed and prepared for sequencing (e.g., being read). As part of the preparation process, multiple copies of the DNA sequence may be generated. In an example, an amplification system 115 of the data storage system 100 may ensure that multiple copies of the DNA data are generated.

A sequencing system 120 may then be used to read DNA sequences from the dense storage system 135. In an example, the sequencing system 120 determines and/or identifies an order of the DNA symbols (e.g., ACTG) in a DNA segment of a DNA sequence that is being read. The sequencing system 120 may use a variety of sequencing methods such as, for example, sequencing by synthesis, nanopore sequencing, and the like.

Once the DNA sequence has been read, a decoding system 125 maps the DNA symbols (e.g., in base-4) back to digital data (e.g., in base-2). For example, in "direct decoding," if the decoding system 125 receives CATGCA as the DNA sequence, the decoding process performed by the decoding system 125 would return 010010110100 (e.g., using the corollary of the binary-to-quaternary mappings discussed above) to a requesting computing device (e.g., computing device 150). Other more complex decoding processes are described herein. In some examples, the inverse of the encoding process used to make the DNA sequence may be used as the decoding process.

In some examples, errors may occur during the synthesis process, the storage process and/or the sequencing process. These errors may be, for example, insertion and deletion ("indel") errors and/or substitution errors. For example, during a synthesis process in which the DNA sequence CATGCA is being synthesized, one or more symbols may be deleted or lost during the creation of the DNA molecule. As a result, a DNA sequence CTGCA may be stored by the dense storage system 135. In another example, during a synthesis process in which the DNA sequence CATGCA is being synthesized, an additional symbol may be added. As a result, a DNA sequence CCATGCA may be stored by the dense storage system 135. Although a single insertion error and a single deletion error are discussed, multiple deletions and/or insertions may occur in a synthesis process. Additionally, these errors may occur during storage and/or during a sequencing process (e.g., during the writing/creating of the DNA molecule, or during the reading/sequencing of the DNA molecule).

In yet another example, during a synthesis process in which the DNA sequence CATGCA is being synthesized, the synthesis system 110 may substitute one symbol for another. As a result, a DNA sequence TATGCA may be stored in the dense storage system 135 instead of the DNA sequence CATGCA. In an example, multiple substitution errors (along with one or more indel errors) may occur during the synthesis process, during storage and/or during a sequencing process.

In order to address the above, the data storage system 100 may include an error correction system 130. The error correction system 130 may be part of the decoding system 125. The error correction system 130 may use various processes to detect and address indel errors and/or substitution errors. In one example, indel errors may be addressed by generating multiple copies of a particular DNA sequence. Once generated, each of the copies of the DNA sequence are read and compared to generate a consensus codeword. For example, a first DNA symbol (or DNA segment consisting of multiple DNA symbols) of a first DNA sequence is compared with a first DNA symbol (or DNA segment consisting of multiple DNA symbols) from one or more of the copies of the DNA sequence. This process repeats for each DNA symbol (or DNA segment) in the DNA sequence.

The error correction system 130 may then determine, based on consensus data across all of the copies, which DNA symbol is the correct (or most correct) DNA symbol for that particular index (or DNA segment). For example, the most prominent DNA symbol in each index of the DNA sequence may be selected as the correct DNA symbol and a consensus codeword is generated for each DNA segment. The resulting consensus codeword is mapped to corresponding ones and zeros and is provided to the decoding system 125 (e.g., a low-density parity check (LDPC) decoder).

In an example, the consensus data generated by the error correction system 130 may be referred to herein as hard bit data or hard information. The error correction system 130 and/or the decoding system 125 described in the present application may also generate and use soft-bit data or soft information using information associated with the consensus data (or using information that is obtained while the consensus data is determined).

For example, once multiple copies of a particular DNA sequence have been copied or otherwise generated (e.g., by the amplification system 115), each copy of the DNA sequence that is associated with a received codeword (e.g., DNA-based data that is to be read from the dense storage system 135), is divided into p DNA segments (where p is equal to or greater than two). Each DNA segment has a DNA segment length q (where q is equal to or greater than one).

For example, the DNA sequence CATGCA may be divided into two different DNA segments having a length of three. As such, a first DNA segment may be "CAT" and a second DNA segment may be "GCA". In another example, the DNA sequence CATGCA may be divided into three different DNA segments having a length of two. In this example, the first DNA segment would be "CA", the second DNA segment would be "TG" and the third DNA segment would be "CA". In yet another example, the DNA sequence CATGCA may be divided into six different DNA segments having a length of one. In this example, the first DNA segment would be "C", the second DNA segment would be "A", the third DNA segment would be "T", the fourth DNA segment would be "G" and so on. The position of each DNA symbol in each DNA segment is referred to as an index. Thus, in the DNA segment "CAT", "C" is the first index, "A" is the second index and "T" is the third index.

Corresponding DNA segments for each copy of a DNA sequence associated with a codeword (or data to be read) are compared to determine: 1) a ratio of DNA symbols in agreement in each index of each of the DNA segments; and/or 2) whether a length of each of the DNA segments are the same. Using this information, soft bit information (or the log likelihood ratio (LLR)) of that particular consensus codeword (e.g., a DNA segment, a DNA symbol, a series of bits, or a bit), may be generated. In some examples, a single LLR value may be generated for an entire consensus codeword. In another example, each bit(s) or DNA symbol in a particular DNA segment may be analyzed separately to determine an LLR for that DNA symbol or bit.

The data storage system 100 may also include a dense storage management system 140. In an example, the dense storage management system 140 controls the various operations and/or processes that are carried out by and/or on the dense storage system 135. The operations and/or processes may include the mechanics of storage and retrieval of the DNA data and/or information storage management (e.g., making copies of data, deleting data, selecting subsets of the data, etc.). The dense storage management system 100 may also store the various LLR values described above.

The data storage system 100 may also include a control system 145. The control system 145 may include at least one processor, at least one controller and/or other such control circuitry. The control system 145 may include circuitry for executing instructions from the computing device 150 (or from another source) and/or providing instructions to the various subsystems of the data storage system 100. The control system may also cause the error correction system 130 and/or the decoding system 125 to pause or stop a decoding process in order to update the various LLR values described above.

This process of converting the input data (base-2) into DNA molecule(s) (base-4) and subsequently converting the DNA molecule(s) (base-4) into output data (base-2), including any of the interim processes that the data and/or DNA molecules undergo, may be referred to herein as "the DNA storage channel." It should be understood that, in these examples, it is an objective of the DNA storage channel and the systems and methods described herein to generate output data that is as close to identical to the input data as possible.

Figure 2:
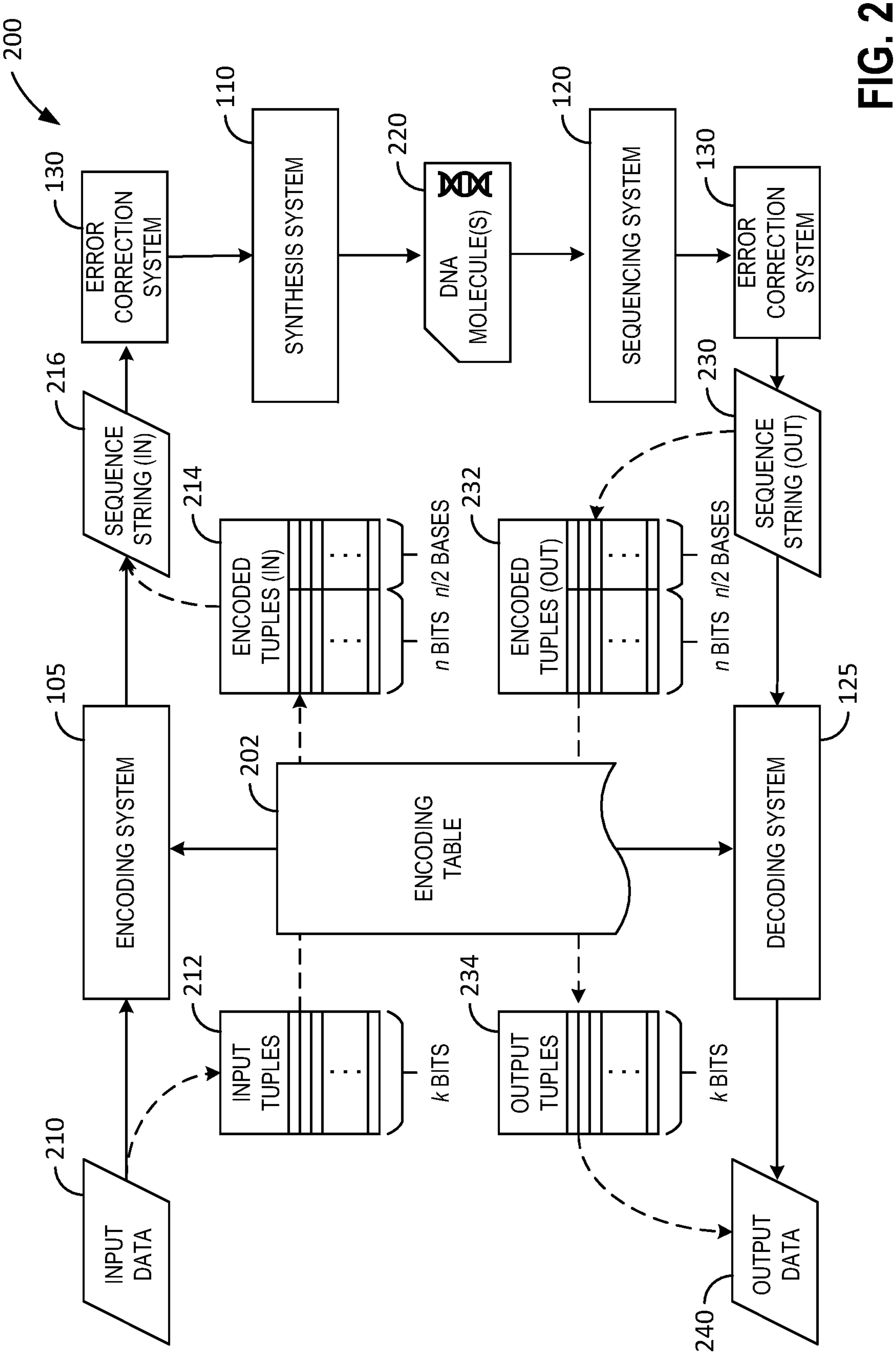
FIG. 2 is an example DNA storage system that provides encoding and decoding data in a DNA storage channel for improved accuracy and reduced error rates.

FIG. 2 is an example DNA storage system 200 that provides encoding and decoding data in a DNA storage channel for improved accuracy and reduced error rates. In some examples, components of the DNA storage system 200 may be similar to components of the DNA storage system 100 of FIG. 1. In this example, the encoding system 105 prepares input data 210 for memorialization (e.g., storage) in DNA form, with the synthesis system 110 performing the actual creation of DNA molecules 220. In other words, the encoding system 105 manipulates the input data 210 to prepare an input sequence string (or "sequence string (in)") 216 that is then used by the synthesis system 110 to create one or more DNA molecules 220 that "write" or "store" the underlying data. The sequencing system 120 is also configured to "read" the DNA data (e.g., by sequencing the DNA molecule(s) 220) to generate a sequence string 230 (or "sequence string (out)") 230 that is then used by the decoding system 125 to generate output data 240.

For purposes of these examples, the input data 210 and the output data 240 are considered strings of data (e.g., long sequences of binary bits). Further, the DNA storage system 200 and associated processes described herein are configured to recreate the input data 210 in the form of the output data 240 by way of DNA molecules 220. In other words, though there are numerous ways in which errors can get introduced into a DNA storage channel, in an error-free situation, the output data 240 would be identical to the input data 210, and any deviation from that ideal typically indicates some type of error having occurred in the channel. Additionally, an encoding table 202 is presumed to be already created during the operations illustrated in FIG. 2. Greater details with regard to the structure of the encoding table 202 are described below in FIGS. 3A-3D, and FIGS. 4A-5 provide additional details and examples on how the encoding table 202 is created and used.

In the example, the DNA storage system 200 uses the encoding table 202 to prepare the input data 210 for synthesizing into DNA molecule(s) 220 (e.g., for storing the input data 210 within DNA), and likewise for sequencing those DNA molecules 220 and decoding the data using the encoding table 202 to generate the output data 240. This series of data manipulations, synthesis, and sequencing represents a DNA storage channel. The encoding table 202 includes a list of mappings that are used to convert various input segments of data (e.g., short strings of bits) into various encoded segments of data (e.g., short strings of bits or bases) during encoding, and vice versa during decoding. These mappings act as a code for translating chunks of the input data 210 (e.g., in binary, or base-2) into chunks of DNA data (e.g., in the quaternary, or base-4 system of DNA nucleotides A, T, G, and C) that can then be memorialized in the DNA molecules 220.

More specifically, before performing encoding of the input data 210, the encoding system 105 breaks up the input data 210 into an ordered list of input tuples 212. For purposes of discussion, the size of each of the input tuples 212 is k bits (e.g., binary, base-2) and, as such, the input tuples 212 have a domain of $2^k$ possible distinct values (e.g., from all 0's to all 1's). In the various examples provided herein, k is 6 bits. As such, the input tuples 212 represent an ordered list of the first six bits of the input data 210, the second six bits of the input data 210, and so on.

The encoding system 105 converts each of these input tuples 212 into encoded tuples 214 based on the contents of the input tuples 212. The encoded tuples 214 are provided in a larger domain than the input tuples 212. For purposes of discussion, the size of each of the encoded tuples 214 is n bits (e.g., in base-2) or n/2 bases (e.g., in base-4) and, as such, the encoded tuples 214 have a domain of 2n possible distinct values, and where $k<n$ and $2^k<2'$. The examples provided herein may include either or both the binary base-2 notation for an encoded tuple 214 and the DNA base-4 representations of the encoded tuple 214, where the base-2 and base-4 representations of a given encoded tuple 214 are related using a straight encoding of A=00, T=01, G=10, and C=11 (or other such straight base-2 to base-4 encoding). In the various examples provided herein, n is 8 bits (e.g., 4 bases). As such, the encoded tuples 214 represent an ordered list of encoded versions of each of the corresponding input tuples 212.

The encoding table 202 thus includes $2^k$ mappings, one for each unique binary number that can occur in the $2^k$ domain space of the input tuples 212. More specifically, each mapping includes one of the $2^k$ possible binary numbers in the $2^k$ domain space as well as a single binary number and/or a base-4 DNA segment in the $2^n$ domain space of the encoded tuples 214. For purposes of discussion, the domain space of the input tuples 212 is referred to herein as the "input domain" and the domain space of the encoded tuples 214 is referred to herein as the "encoded domain." Further, the binary numbers of the input domain may be referred to herein as "input segments" (e.g., "000000", "000001", . . . , "111111"), and the binary numbers of the encoded domain, or their associated base-4 DNA representations, may be referred to herein as "encoded segments" (e.g., "00000000"/"AAAA", "00000001"/"AAAT", . . . , "11111111"/"CCCC"). It should be understood that each mapping in the encoding table 202 is a one-to-one mapping between an input segment in the input domain and an encoded segment in the encoded domain, and a mapping is included for every input segment in the input domain.

For example, one mapping in the encoding table 202 may be defined between the input segment 010001 and the encoded segment 00111011 (ACGC). As such, whenever the encoding system 105 encounters an input tuple 212 of 010001, then the associated encoding tuple 214 is created as 00111011 (ACGC). Similarly, since each of the possible input segments in the input domain have a mapping defined in the encoding table 202 to one and only one encoded segment in the encoded domain, for each input tuple 212 of the input data 210, the encoding system 105 looks up the associated encoded segment based on the contents of that input tuple 212 (e.g., as one of the possible $2^k$ input segments) and places that encoded segment as the next encoded tuple 214.

Once all the input tuples 212 have been converted into encoded tuples 214, the encoding system 105 generates a sequence string 216 from the encoded tuples 214. More specifically, in the example, the encoding system 105 concatenates the DNA base-4 base pair representations of each of the encoded tuples 214 in sequential order to generate the sequence string 216. This sequence string 216 is then used by the synthesis system 110 to generate one or more DNA molecules 220. In the example, the sequence string 216 is first processed by the error correction system 130 (e.g., an ECC encoder) before synthesis, which may, for example, add parity data, error correction codes, cyclic redundancy check (CRC) signature, or other data that can be used to improve error rates or authenticity upon reading the data. In another example, the error correction system 130 may be positioned prior to the encoding system 105 (e.g., the input data 210 may already include any parity or ECC data prior to the encoding). In another example, no error correction system 130 may be implemented. Accordingly, in the example, the input data 210 is thus encoded, synthesized, and stored in the DNA molecule(s) 220. The data in this form may be referred to herein as the "DNA data."

To extract the data from the DNA molecule(s) 220, the sequencing system 120 sequences the molecule(s) 220. This sequencing operation produces the sequence string 230 (e.g., a string of DNA bases, in base-4 representation, and may include or otherwise be converted to base-2 representation). In the example, the error correction system 130 may perform any error correction techniques after sequencing (e.g., using the parity data or error correction codes on the sequencing output, based on whichever error correction processes were performed prior to synthesis). In examples where error correction was performed before encoding, then the complementary error correction occurs after decoding. In this example, at this stage, the decoding system 125 then decodes the sequence string 230 using the encoding table 202. More specifically, the decoding system 125 breaks up the sequence string 230 into an ordered list of n-bit (or n/2 DNA bases) encoded tuples (or "encoded tuples (out)") 232. Each of these encoded tuples 232 is then converted into an associated output tuple 234 using the mappings of the encoding table 202. For example, and like the reverse of the encoding process discussed above, when an encoded tuple 232 of 00111011 (ACGC) is decoded, the decoding system 125 identifies the mapping that includes an encoded segment of 00111011 (ACGC), identifies the associated input segment of 010001, and creates an output tuple 234 with 010001 as the output segment for that output tuple 234. Once all of the encoded tuples 232 have been similarly decoded into the output tuples 234, the decoding system 125 generates the output data 240 from the output tuples 234 (e.g., performing in order concatenation of each of the output tuples 234).

FIG. 3A to FIG. 3D illustrate an example encoding table 300 that may be used by the DNA storage system 200 of FIG. 2. In some examples, the encoding table 300 may be similar to the encoding table 202 of FIG. 2. In the example shown here, portions of the encoding table 300 are distributed amongst each of the FIGS. 3A-3D. More specifically, the first set of 64 entries of the encoding table 300 (e.g., indexes 0 to 63) are shown in FIG. 3A, the second set of 64 entries (e.g., indexes 64 to 127) are shown in FIG. 3B, the third set of 64 entries (e.g., indexes 128 to 191) are shown in FIG. 3C, and the fourth set of 64 entries (e.g., indexes 192 to 255) are shown in FIG. 4C. Further, on each of FIGS. 3A-3D, the 64 entries are broken up into left and right portions, with the left portion being the lower valued indices and the right portion being the higher valued indices.

In the example, the encoding table 300 is used to address the example input domain of k=6 bits and the example encoded domain of n=8 bits (4 bases). The encoding table 300 includes four columns, namely an index column (or just "index" when referring to a particular entry) 310 (identified by column heading "#"), a base-2 encoded segment column (or just "base-2 encoded segment" when referring to a particular entry) 312 (identified by column heading "BASE-2"), an encoded segment base-4 column (or just "base-4 encoded segment" when referring to a particular entry) 314 (identified by column heading "BASE-4"), and an input segment column 316 (identified by column heading "k-BIT"). As such, each row 320 of the encoding table 300 thus includes an index 310, a base-2 encoded segment 312, a base-4 encoded segment 314, and an input segment 316.

In the example, each index 310 is a unique number that is used as a unique identifier for that particular row 320. Here, the indexes 310 are represented in base-10 and range between 0 and 255. For purposes of convenience, the various rows 320 of the table 300 may be identified herein by their index number.

Each base-2 encoded segment 312 is an n-bit (e.g., 8-bit) string in base-2 representation. In this example, the index 310 for each row is the base-10 representation of the base-2 encoded segment 312, though this is not necessary to perform the systems and methods described herein. Each base-4 encoded segment 314 is an n/2-base (e.g., 4 DNA bases) string in DNA base-4 representation, where the base-4 encoded segment is merely a direct translation of each two bits of the base-2 encoded segment into an associated DNA base. Further, it should be noted that the encoding table 300 includes one row 320 for each unique base-2 encoded segment 312, and thus for each unique base-4 encoded segment 314. As such, since there are $2^8$ unique combinations in the encoded domain (e.g., 2n, where n=8), there are thus $2^8$ (256) rows in the encoding table 300, one for each unique encoded segment 312.

The input segment column 316, in the example, is used to store the unique input segments in the k-bit input domain (e.g., 6-bit numbers, base-2). Each unique input segment of the $2^6$ (64) unique input segments in the input domain (e.g., $2^k$, where k=6) appear in one and only one of the rows 320 of the table 300.

It should be noted that some of the input segments 316 provided a 6-bit base-2 input segment (e.g., rows 33-36 of FIG. 3A), while other rows provide a character-based code. When a particular row 320 includes a 6-bit base-2 number in the input segment column 316, that row has been configured as a mapping between that 6-bit base-2 input segment and the 8-bit base-2 encoded segment 312 (4-bases DNA base-4 encoded segment 314) of that same row. When a particular row 320 includes a character-based code, that row is not used as a mapping. The character codes appearing in the input segment column 316 represent a reason why that particular row was excluded as a mapping. In this example, the code "REP" (e.g., "repeating") indicates that the DNA base-4 encoded segment 314 of that row has at least one adjacent repeating pair of bases (e.g., an "AA", a "TT", a "GG", or a "CC"), and thus was excluded under that exclusion criterion (e.g., "use no rows that have adjacent bases"). Similarly, the code "T" (e.g., "T-base") indicates that the DNA base-4 encoded segment 314 of that row has a "T" in either the first or second positions (from most significant to least significant), and thus was excluded under that exclusion criterion. It should be understood that the character codes appearing the non-mapping rows of the table 300 are included in FIGS. 3A-3D for purposes of discussion and may or may not be stored in the encoding table 300. Exclusion criteria are discussed in greater detail below with respect to FIGS. 4A-5.

As such, since there are $2^8$ (256) rows in the table 300 and only $2^6$ (64) mappings are needed to address each unique input segment of the input domain, the table 300 has 64 rows that map an input segment to an encoded segment, and the other 192 rows are unused or "excluded" from the mapping functionality provided by the DNA storage system 200.

Figure 4A:
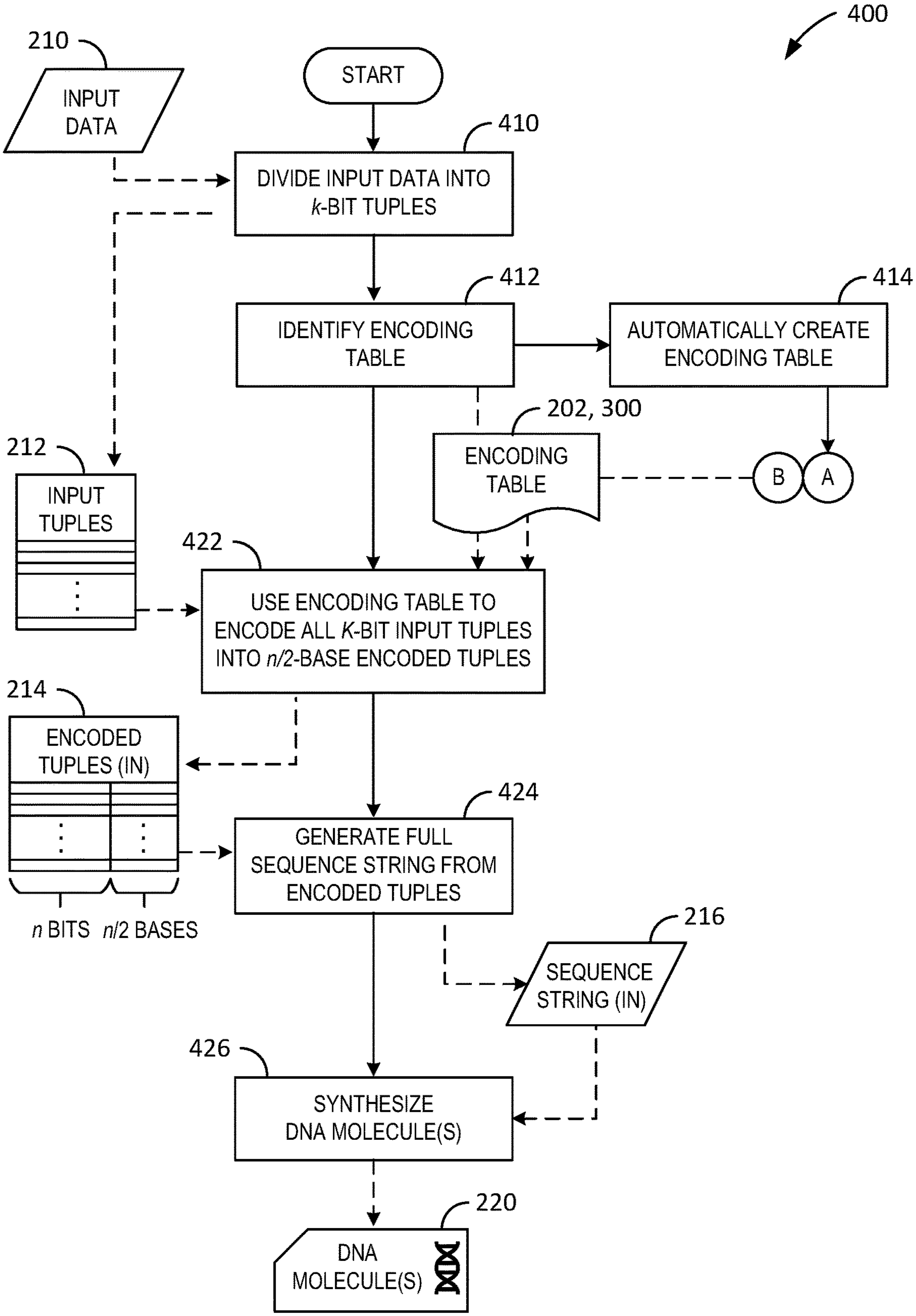
FIG. 4A and FIG. 4B illustrate a flow chart of an example method for encoding the input data prior to synthesizing one or more DNA molecules.
Figure 4B:
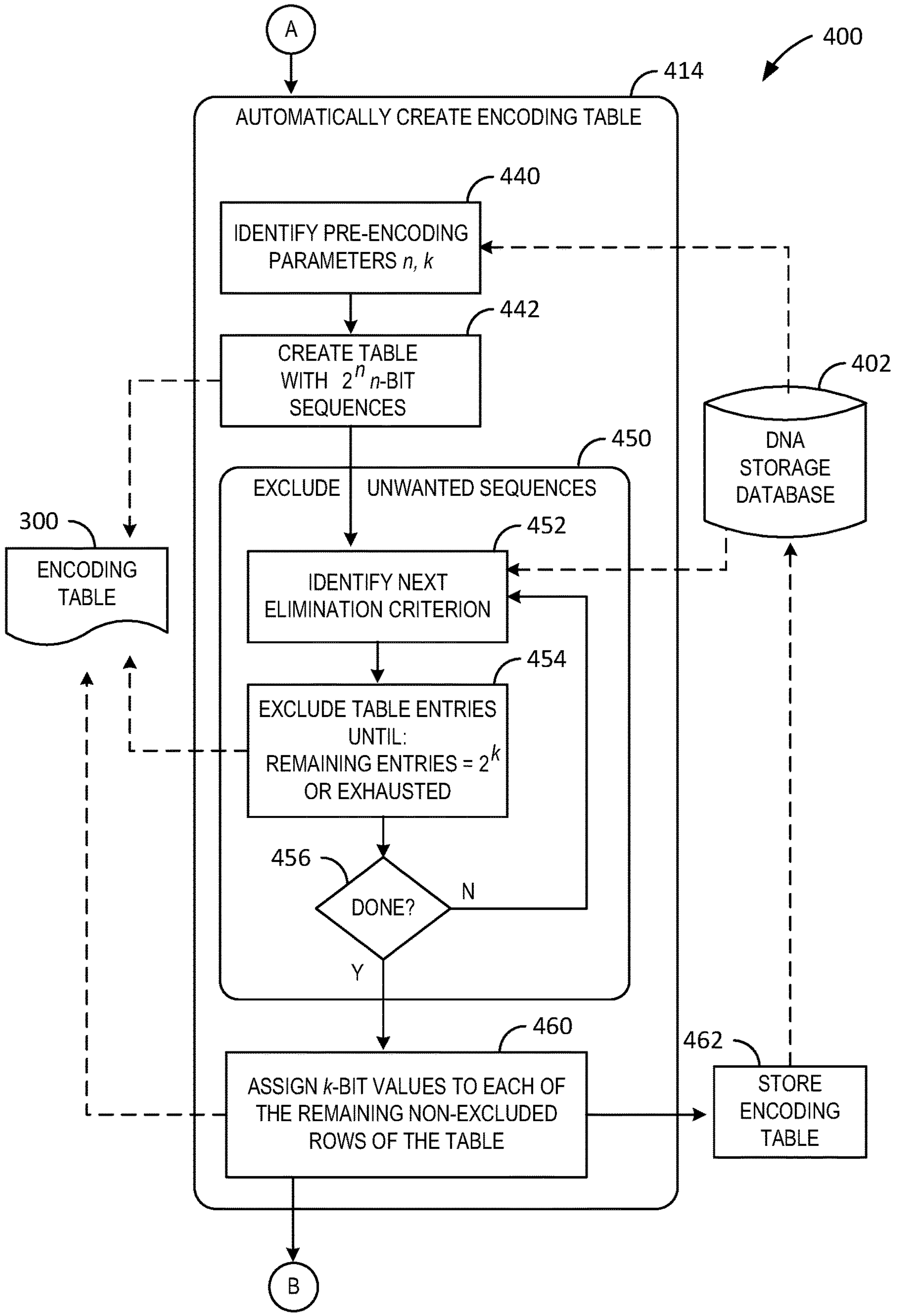

FIG. 4A and FIG. 4B illustrate a flow chart of an example method 400 for encoding the input data 210 prior to synthesizing one or more DNA molecules 220. In some examples, the method 400 may be performed by the computing device 150 and components of the DNA storage subsystem 102 shown in FIG. 1, as a part of the DNA storage system 200 shown in FIG. 2, or the like. In this example, the various operations are performed by encoding system 105 or the synthesis system 110 of FIG. 2, executing on the computing device 150 and associated components of the DNA storage system 100 of FIG. 1, and using the encoding table 300 of FIGS. 3A-3D.

Referring now to FIG. 4A, in the example, at operation 410, the encoding system 105 divides the input data 210 into an ordered sequence of k-BIT "input tuples" 212 (e.g., chunks or segments of k bits each). In this example, the input data 210 is represented as a sequential string of ordered bits, and operation 410 segments the input data 210 into 6-bit input tuples 212. For example, the first 6 bits of the input data 210 is assigned to the first input tuple 212, the next 6 bits of the input data 210 is assigned to the second input tuple 212, and so on until all bits of the input data 210 have been processed into input tuples 212. For example, if the input data 210 is 3 megabytes (MB) in size (e.g., 3,145,728 bytes, or 25,165,824 bits), then the input tuples 212 would include (25,165,824/6)=4,194,304 6-bit input tuples.

At operation 412, the encoding system 105 identifies the encoding table 300. In some examples, the encoding table 300 may be pre-existing (e.g., previously created, stored, and retrieved from a DNA storage database 402). For example, a storage administrator may identify one or more exclusion criteria and may manually create the encoding table 300 by assigning each of the 64 possible input segments (e.g., $2^k$ unique segments, where k=6) to one of the particular rows 320 of the table 300 while avoiding encoded segments 314 that manifest one or more of the exclusion criteria.

In some examples, the encoding system 105 may dynamically (e.g., automatically) create the encoding table 300 (e.g., based on input parameters, one or more exclusion criteria, or such). For example, at operation 414, the encoding system 105 automatically creates the encoding table 300. These examples are referred to herein as "dynamic table creation."

FIG. 4B illustrates sub-operations associated with the automatic creation of the encoding table 300 of operation 414. Referring now to FIG. 4B, when creating the encoding table 300, the encoding system 105 identifies pre-encoding parameters at operation 440. In this example, the parameters include the variables k and n, which are used to define the size of the input domain and the size of the encoded domain, respectively. In some examples, some or all of the parameters may be retrieved from the DNA storage database 402. At operation 442, the encoding system 105 creates the encoding table 300. More specifically, the encoding table 300 is initially created with 2n rows, with each row being assigned a unique index 310 and populated with a unique n-bit base-2 encoded segment 312 and associated n/2 DNA base encoded segment 314.

At operation 450, in the example, the encoding system 105 excludes unwanted sequences from the encoding table 300 (e.g., based on exclusion criteria). More specifically, operation 450 includes several sub-operations in this example. At operation 452, an exclusion criterion is identified. Exclusion criteria provide criteria, such as unwanted properties or patterns relative to the contents of the DNA base-4 encoded segments 314. In some examples, search criteria (e.g., regular expressions, using "regex" syntax) may be included in exclusion criteria, allowing the encoding system 105 to test encoded segments 314 against those search criteria. At operation 454, the encoding system 105 uses the current exclusion criterion to identify table entries (e.g., rows 320) in the table 300 (e.g., one at a time) and mark those rows as excluded until either all of the matching rows 320 in the table 300 that match this exclusion criterion have been excluded, or until the number of remaining (e.g., non-excluded) rows 320 in the table 300 total $2^k$ (e.g., 64, the target number of entries in the table 300 needed for mapping). In some examples, the encoding system 105 may maintain a loop counter for the number of non-excluded rows 320 remaining in the table 300 (e.g., counting down from 2$n$ as rows 320 get excluded, terminating at a count of $2^k$) or, conversely, a loop counter for the number of excluded rows 320 (e.g., counting up from zero as rows 320 get excluded, terminating at a count of $(2^n-2^k)$.

At operation 456, the encoding system 105 evaluates whether or not the exclusion operation 450 is done. In the example, operation 456 terminates the exclusion of further rows when either the loop counter described above has reached its limit (e.g., indicating that, in either case, only $2^k$ (64) rows remain not excluded in the table 300) or if there are no further elimination criteria identified for this operation 450. In situations where all of the elimination criteria have been processed by operation 450 but there remain more than $2^k$ non-excluded rows in the table 300 at this stage, the encoding system 105 excludes additional rows until the number of remaining non-excluded rows is $2^k$ (e.g., keeping the first $2^k$ remaining non-excluded rows, randomly removing rows, or the like).

If, at operation 456, the number of remaining non-excluded rows in the table 300 is greater than $2^k$ and there is at least one remaining elimination criterion, the operation 450 returns to operation 452, identifying the next elimination criterion and continuing to eliminate table entries. In some examples, a prioritized (e.g., ordered) set of multiple elimination criteria may be defined.

In this example, the first (or primary) elimination criterion involves removing any rows 320 that have repeating adjacent base pairs (e.g., any base-4 encoded segments 314 that include "AA", "TT", "GG", or "CC"). During the first iteration of operation 450, all of the rows that match this criterion are excluded and are marked as such with the "REP" identifier appearing in the input segment column 316 of FIGS. 3A-3D.

The second elimination criterion in this example involves excluding any rows 320 that have any "T" bases, and favoring excluding rows 320 when "T's" appear earlier in the associated encoded segments 314). For example, this exclusion criterion may first be processed by removing encoded segments 314 that start with "T" (e.g., "T*") and, if there are more row exclusions needed, then proceeding to removing encoded segments 314** that have a "T" in second position (e.g., "*T"), and so forth for the remaining positions. In another example, this exclusion criterion may remove encoded segments 314 based on the number of T bases appearing in the encoded segments 314 (e.g., from highest to lowest), thus favoring the exclusion of rows 320 that use more T bases. During this second iteration of operation 450, only some of the rows that match this criterion are excluded and are marked as such with the "T" identifier appearing in the input segment column 316 of FIGS. 3A-3D (unless they were already excluded with a prior criterion). More specifically, all of the rows 320 that start with a T base (e.g., "T*") are marked for exclusion under this criterion (e.g., all of the remaining rows 64 to 127 of FIG. 3B). After processing the "T***" rows, the elimination of second position T rows (e.g., "*T") is processed. However, during this processing, the loop counter reaches its target of $2^k$, and thus ceases the exclusion process at that time. More specifically, all remaining non-excluded rows in FIG. 3**A matching the "*T" pattern are marked for exclusion (e.g., rows 17-19, 24, 25, and 27-30). Continuing on, all of the rows of FIG. 3B have been excluded by this time, so no further exclusion occurs there. In FIG. 3**C, several of the matching rows matching the "*T" pattern are marked for exclusion (e.g., rows 145-147, 152, 153, and 155-157). However, it is at row 157 when the $2^k$ limit is reached. As such, the exclusion operation 450** is terminated at this time (e.g., not excluding some rows that match the "*T" pattern, such as row 158 and numerous rows on FIG. 3**D).

In this example, operation 450 terminated at the $2^k$ limit before completing all of the elimination criteria. Not only did the second elimination criterion have unprocessed rows, but this example may have included additional criteria. For example, a third elimination criterion may have identified rows that include high "GC" content, which can include "GC" pairings or "CG" pairings anywhere in the encoded segment 314, and may include situations where at least one G and at least one C occur (e.g., "C*GG"). In some examples, this high GC content may be scored based on a total number of G's and C's appearing in the encoded segment 314 when at least one G and at least one C appear.

When the operation 450 is indicated as complete (e.g., in sub-operation 456), the encoding table 300 should have ($2^n$-$2^k$) of the rows marked as excluded (or otherwise removed) and, more significantly, should have $2^k$ non-excluded rows. In this example, 192 rows 320 are excluded and 64 of the rows remain non-excluded. It is these non-excluded rows that are the rows that will be configured for use the encoding and decoding performed by the method 400.

More specifically, it is at operation 460 that these $2^k$ non-excluded rows are configured as mapping rows for the input data. Each of the remaining non-excluded rows is configured with one of the $2^k$ unique k-bit values, and that particular k-bit string is stored in the input segment column 316 of the table 300. In this example, operation 460 beings at the first non-excluded row of the table 300 (e.g., row 33 on FIG. 3A) and begins assigning unique 6-bit values. For example, row 33 is assigned to "000000" (base-2), row 34 is assigned to "000001", row 35 is assigned to "000010", and so on. As such, this assignment process of operation 460 continues until all $2^k$ unique k-bit values are assigned to one of the $2^k$ non-excluded rows, thus completing the creation of the table 300. The assignments of operation 460 thus create mappings between 6-bit input segments 316 and 8-bit (4-base) encoded segments 312, 314. At operation 462, the table 300 may be stored in the DNA storage database 402. As such, the automatic encoding table creation operation 414 concludes and may return to FIG. 4A.

In some examples, the operation 450 of excluding unwanted sequences may utilize scoring or weighting between multiple elimination criteria, thus combining both multi-criteria consideration and providing a relative importance to each criterion in that consideration. Consider the three example criteria of contiguous bases, T bases, and GC content provided above. In that example, the GC content criterion was never triggered because the exclusion process terminated before getting to that third criterion. To provide more integrated and weighted flexibility, in some examples, the operation 450 may generate a score for each row 320 of the table 300. For example, each row 320 may be evaluated as to how many of the exclusion criteria that row 320 matches (e.g., where the score for each row is the number of matching exclusions). As such, after the scoring, the exclusion of table entries may start with the elimination of the highest scoring rows and continuing to eliminate lower scoring rows (e.g., the rows that match 3 criteria may be excluded first, then the rows that match 2 criteria, then 1 criterion) until one of the termination conditions is satisfied. In some examples, each elimination criterion may also have an associated weight that is used to configure a relative importance or significance between the criteria, and these weights may be used in the scoring.

Returning again to FIG. 4A and identifying the encoding table at operation 412. In some examples, the encoding system 105 may dynamically determine which encoding table 300 to use, from multiple pre-determined encoding tables, based on the contents of the input data 210. These examples are referred to herein as "dynamic table selection."

During dynamic table selection, identifying the encoding table at operation 412 may include, for example, determining an amount of "GC" content that appears in the input data 210 and selecting a particular table 300 based on that GC content value. For example, if there is a low amount of GC content in the input data 210, then the encoding system 105 may be configured to select a table 300 that has been configured to increase GC content (e.g., to be within a target range), as with certain technologies, a low level of GC content can increase the error rate. If there is a moderate or average amount of GC content (e.g., within a target range), then the encoding system 105 may select a table 300 that has been configured without concern to shaping toward or away from GC content (e.g., did not use that elimination criterion), or that adds as about as much GC content as it removes (e.g., based on a comparison between GC content of the input tuples as compared to the GC content of the current encoded tuples). In situations where there is a high amount of GC content detected, then the encoding system 105 may select a table 300 that has been configured to shape away from GC content (e.g., where the GC elimination criterion was the primary elimination criterion or a significantly utilized secondary elimination criterion).

To determine the GC content value for the input data 210, the encoding system 105 may, for example, count the number of lines that include at least one G base and one C base, and this count may be used as the GC content value for distinguishing between which of the tables 300 to use. In some examples, the count may further be weighted based on additional G's and C's. For example, a tuple 214 with one G and one C may add a count of 1.0, where another tuple with two Gs and one C may add a count of 2.0 (e.g., weighted count=(num_Gs+num_Cs), in tuples with at least one G and at least one C). As such or similarly, tuples with more G's and/or C's can be weighted with a higher likelihood to be removed from use in the encoding. In some examples, this weighted or unweighted GC content value may be normalized (e.g., to a percentage, to a 0.0 to 1.0 range, or the like) based on the size of the input data, thereby allowing the encoding system 105 to calibrate the weighting based on different size inputs.

In this dynamic table selection example, one or more thresholds may be preconfigured for use with two or more tables 300. For example, in a two table 300 example, one threshold may be provided (e.g., if the percentage of GC content in the input data 210 is under 15%, use a first table 300, otherwise use a second table 300). In a three table 300 example, two thresholds may be provided (e.g., if GC content is under 10%, use a first table 300, or if between 10% and 20%, use a second table, otherwise if more than 20%, use a third table), where the two thresholds may identify the opposite ends of a target range for GC content.

In some dynamic table selection examples, the tables 300 may also be dynamically created. In such examples, and in addition to the threshold(s), the encoding system 105 may also receive a number of tables 300 to be created (e.g., instructions to create 2, 3, or more tables), as well as prioritized sets of elimination criteria to associate with each particular table. For example, a first set of elimination criteria for the "under 10% GC content" table 300 may avoid exclusion criteria that eliminate GC content, or may include at least some inclusion criteria that are configured to select encoded tuples with GC content. A second set of elimination criteria for the "10% to 20% GC content" table 300 may promote the exclusion of highly weighted GC tuples (e.g., tuples with 3 or 4 total GC counts), but may relegate minimal GC tuples (e.g., tuples with only one G and only one C) to secondary exclusion (e.g., as a second or third tier elimination criterion). A third set of elimination criteria for the "greater than 20% GC content" table 300 may have the GC elimination criteria as the primary (e.g., first) elimination criteria, with other elimination criteria relegated to second tier or later. As such, the automatic creation of encoding table operation 414 may be performed once for each table 300, and using the particular set of elimination criteria specifically configured for that table.

In some examples, the encoding system 105 may analyze an encoding with a given table 300 (e.g., after operation 422) and may take corrective actions if the encoding does not conform to some predetermined criteria. For example, and regarding the GC content examples, the encoding system 105 may encode the input data 210 with an initial table 300 (e.g., either selected from pre-existing tables or dynamically created, as discussed above) and may then analyze the GC content of the resulting encoded data (e.g., score the GC content value of the encoded tuples 214). If the current GC content value of the encoded data does not satisfy the predetermined criteria (e.g., if the GC content value does not fall within the target range), then the encoding system 105 may alter the composure of the encoding table 300 (e.g., altering which rows 320 of the table 300 are used for mapping). For example, if the GC content value of the current encoded content falls below the target range, then the encoding system 105 may swap out one or more mappings with other rows 320 that have greater GC content. Similarly, if the GC content value falls above the target range, then the encoding system 105 may swap out one or more mappings with other rows 320 that have lower GC content. The row swapping may also consider the other elimination criteria (e.g., by selecting rows 320 not otherwise excluded by the elimination criteria, or by first selecting rows 320 that were eliminated by the least significant of the elimination criteria). The encoding system 105 may then reencode the input data 210 with the updated table 300, and similarly may analyze the resulting table 300 and iterate until the GC content falls within the target range.

At operation 422, the encoding system 105 uses the encoding table 300 to encode each of the input tuples 212 (in k bits) into encoded tuples 214 (in n bits, or n/2 bases). In this example, each 6-bit input tuple 212 is converted into a 4-base encoded tuple 214 using the mappings defined in the encoding table 300. For example, when an input tuple 212 of 011110 is encoded, the encoding system identifies the row of the encoding table 300 that has the input segment 316 that matches this input tuple 212 (e.g., row 179 of FIG. 3C, in this example) and then generates the encoded tuple 214 using the DNA base-4 encoded segment 314 of that row (e.g., "GCAC", in this example). This process, as such, continues generating an encoded tuple 214 for each input tuple 212 until all of the input tuples 212 have been processed. At the end of operation 422, the encoded tuples 214 is an ordered list of encoded tuples. For example, if the input data 210 is 3 MB in size, then the 4,194,304 input tuples 212 would yield the same number of encoded tuples 214 (e.g., 4,194,304 4-base encoded tuples 214). It should be noted that, while the binary representation of each tuple is included in the encoded tuples 214, the encoded tuples 214 do not necessarily need this binary representation (e.g., since only the DNA base-4 encoded segments 314 are eventually used).

At operation 424, the encoding system 105 generates a full sequence string 216 from the encoded tuples 214. In this example, the encoding system 105 concatenates each 4-base encoded tuple 214 together, in order, to generate the sequence string 216. As such, the sequence 216 includes a number of bases equal to the number of encoded tuples times n/2. For example, and continuing the 3 MB example provided above, the total number of bases in the sequence string 216 is (4,194,304*4)=16,777,216 bases.

After the sequence string 216 is generated, the method 400 includes synthesizing one or more DNA molecules 220 using the sequence string 216 at operation 426. This operation 426 may be performed by the synthesis system 110 of FIG. 1. Accordingly, the process of encoding the input data 210 and ensconcing that encoded data by sequencing DNA molecules 220 is complete.

While the above example identifies several types of elimination criteria (e.g., repeating bases, T bases, and GC content) as well as an example hierarchy of importance of each (e.g., first eliminate repeating bases, then onto T bases, then onto GC content), it should be understood that other elimination criteria and other relative ordering of those criteria may be used. Further, while an automated table creation process is provided in FIG. 4B, and as a part of an overall encoding process 400, it should be understood that the encoding table 300 may similarly be manually created using a set of any elimination criteria and any relative ordering.

Further, in some examples, the encoding system 105 may embed a table identifier into the input data 210, into the sequence string 216, or otherwise into the data channel before synthesis. This table identifier is a unique identifier that identifies which particular table 300 was used to encode the data in this particular synthesis (e.g., for this particular DNA molecule 220). The table 300 and its associated table identifier may be stored in the DNA storage database 402. In such examples, the decoding process described below with respect to FIG. 5 may include reading the table identifier (e.g., from the sequence string 230 prior to decoding) and using that table identifier to look up which table 300 to use for decoding that particular DNA molecule 220. In some examples, a CRC signature may be added prior to synthesis. This CRC signature may be used to identify which table 300 to use (e.g., decode with several tables to find which table 300 was used, where the CRC passes only on the correct table).

Figure 5:
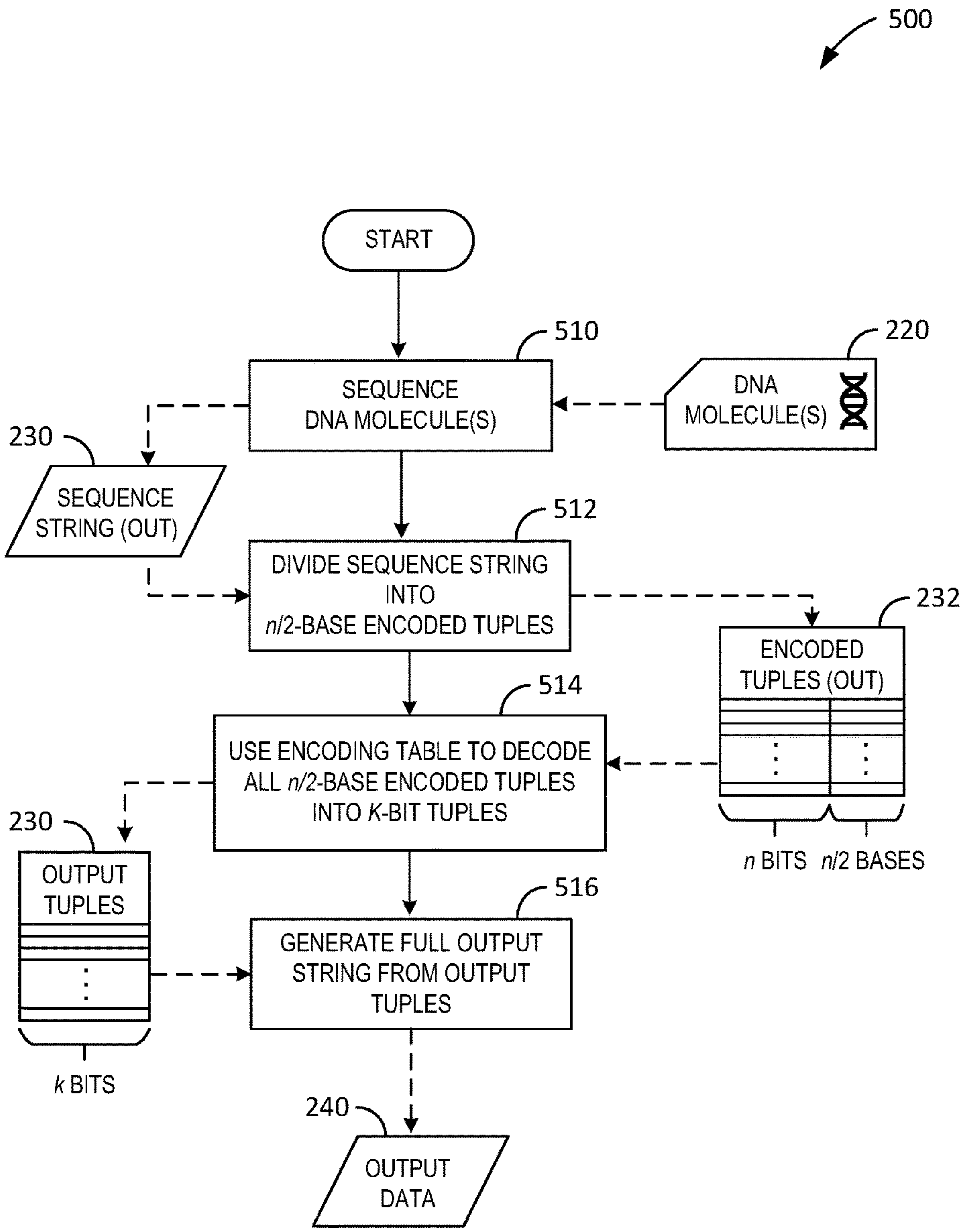
FIG. 5 illustrates a flow chart of an example method for synthesizing the DNA molecules and decoding the encoded data created from the method of FIG. 4A.

FIG. 5 illustrates a flow chart of an example method 500 for synthesizing the DNA molecules 220 and decoding the encoded data created from the method 400 of FIG. 4A. In some examples, the method 500 may be performed by the computing device 150 and components of the DNA storage subsystem 102 shown in FIG. 1, as a part of the DNA storage system 200 shown in FIG. 2, or the like. In this example, the various operations are performed by decoding system 125 or the sequencing system 120 of FIG. 2, executing on the computing device 150 and associated components of the DNA storage system 100 of FIG. 1, and using the encoding table 300 of FIGS. 3A-3D.

In the example, the sequencing system 120 sequences one or more of the DNA molecules 220 at operation 510. This sequencing operation 510 generates the sequence string 230 (e.g., an ordered sequence of bits). Continuing the 3 MB input data example provided above in FIG. 4A, the sequence string 230 is expected to be a string of 16,777,216 bases (e.g., the same size of the sequence string 216, and presuming there no uncorrected errors in the synthesis and sequencing). Ideally, the sequence string (out) 230 is identical to the sequence string (in) 216.

At operation 512, the decoding system 125 divides the sequencing string 230 into encoded tuples 232, which each encoded tuple 232 having n/2 bases. For example, the decoding system 120 may segment the sequence string 230 into encoded tuples 232 of 4 bases each, starting at the beginning of the sequence string 230 and continuing through the end of the string 230. Ideally, if no uncorrected errors are manifested in the DNA channel by this point, the encoded tuples (out) 232 should be the same as the encoded tuples (in) 214 generated during the encoding process. In some examples, the data may be verified (e.g., by CRC) at this stage.

In the example, at operation 514, the decoding system 125 then uses the encoding table 300 (e.g., the same encoding table 300 used in the encoding process 400 that created this DNA molecule 220) to decode all of the encoded tuples 232. In the example, this decoding process operates similar to the encoding operation 422 of FIG. 4A, but in reverse. More specifically, for each encoded tuple 232, the decoding system 125 searches the table 300 to find a row that has a DNA base-4 encoded segment 314 that matches the encoded tuple 232. Once the particular matching row is found, the decoding system 125 generates an output tuple 230 that contains the k-bit input segment 316 of that matching row. For example, if a particular encoded tuple 232 contains the base string "CATG", the decoding system 125 would identify row 198 as the matching row in the table 300. Accordingly, the associated k-bit input segment 316 for that row contains the bit string "100110" and, as such, this bit string is provided in the output tuple 230. Ideally, presuming no errors, the output tuples 230 should be identical to the input tuples 212.

At operation 516, the decoding system 125 uses the output tuples 230 to generate the output data 240. More specifically, in the example, the decoding system 125 concatenates each bit string of the output tuples together, in order, to generate the output data 240. Presuming no errors occur, this output data 240 should be identical to the input data 210.

Figure 6:
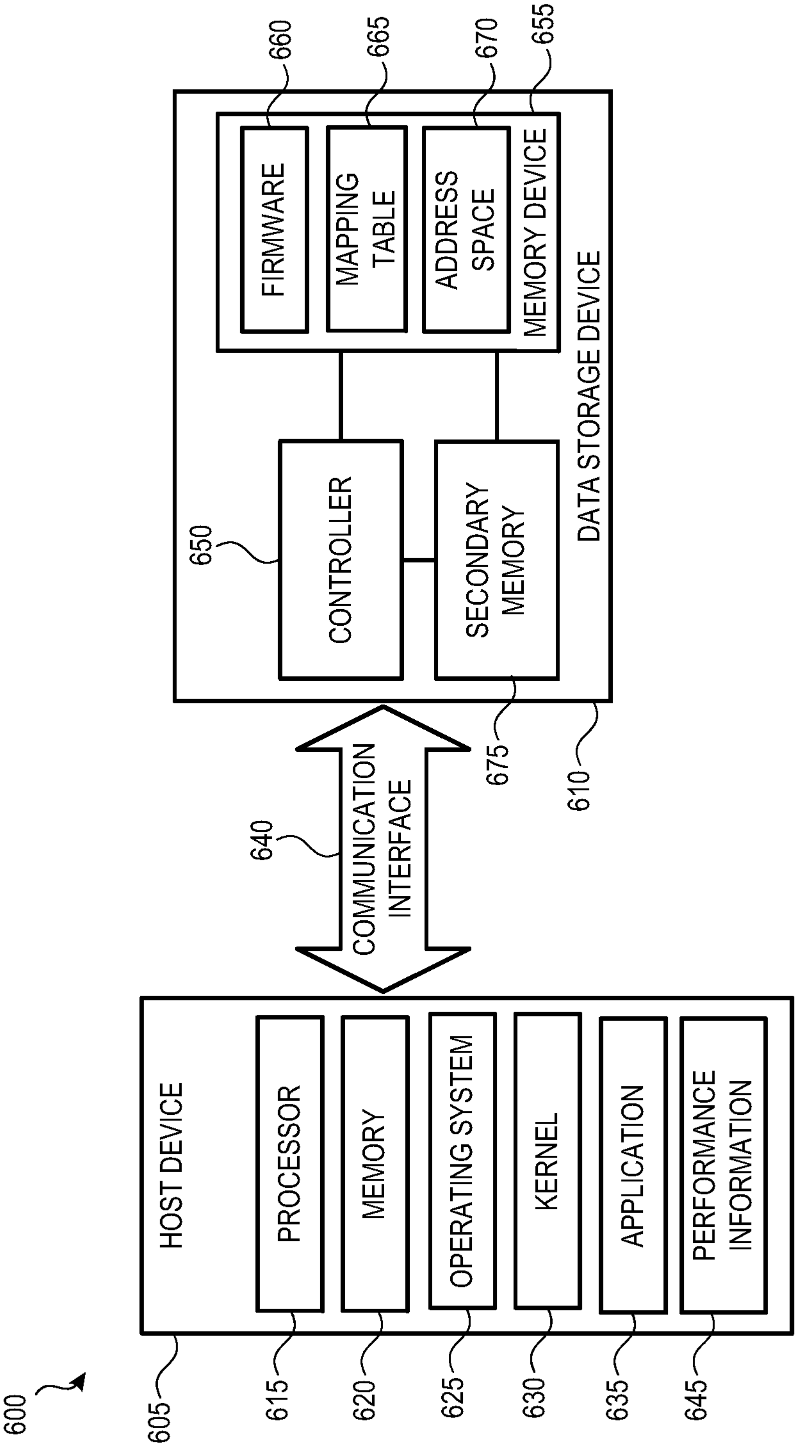
FIG. 6 is a block diagram of a system that includes a host device and a data storage device according to an example.

FIG. 6 is a block diagram of a system 600 that includes a host device 605 and a data storage device 610 according to an example. In an example, the host device 605 may be similar to the computing device 650 shown and described with respect to FIG. 1, and may be used to perform any or all of the operations described herein. The host device 605 includes a processor 615 and a memory device 620 (e.g., main memory). The memory device 620 may include an operating system 625, a kernel 630 and/or an application 635.

The processor 615 can execute various instructions, such as, for example, instructions from the operating system 625 and/or the application 635. The processor 615 may include circuitry such as a microcontroller, a Digital Signal Processor (DSP), an Application-Specific Integrated Circuit (ASIC), a Field Programmable Gate Array (FPGA), hard-wired logic, analog circuitry and/or various combinations thereof. In an example, the processor 615 may include a System on a Chip (SoC).

In an example, the memory device 620 can be used by the host device 605 to store data used by the processor 615. Data stored in the memory device 620 may include instructions provided by the data storage device 610 via a communication interface 640. The data stored in the memory device 620 may also include data used to execute instructions from the operating system 625 and/or one or more applications 635. In an example, the memory 620 is volatile memory, such as, for example, Dynamic Random Access Memory (DRAM).

In an example, the operating system 625 may create a virtual address space for the application 635 and/or other processes executed by the processor 615. The virtual address space may map to locations in the memory device 620. The operating system 625 may include or otherwise be associated with a kernel 630. The kernel 630 may include instructions for managing various resources of the host device 605 (e.g., memory allocation), handling read and write requests and so on.

The communication interface 640 communicatively couples the host device 605 and the data storage device 610. The communication interface 640 may be a Serial Advanced Technology Attachment (SATA), a PCI express (PCIe) bus, a Small Computer System Interface (SCSI), a Serial Attached SCSI (SAS), Ethernet, Fibre Channel, or WiFi. As such, the host device 605 and the data storage device 610 need not be physically co-located and may communicate over a network such as a Local Area Network (LAN) or a Wide Area Network (WAN), such as the internet. In addition, the host device 605 may interface with the data storage device 610 using a logical interface specification such as Non-Volatile Memory express (NVMe) or Advanced Host Controller Interface (AHCI).

The data storage device 610 includes a controller 650 and a memory device 655 (e.g. volatile and/or non-volatile memory). The memory device 655 (and/or portions of the memory device 655) may also be referred to as a storage medium. The memory device 655 includes a number of storage elements. In an example, each storage element is a chip or a memory die that is used to store data.

For example, the memory device 655 may include a first memory die and a second memory die. In an example, the first memory die and the second memory die include non-volatile memory elements such as, for example, NAND flash memory elements and/or NOR flash memory elements. Although two memory dies are mentioned, the memory device 655 may include any number of storage elements. For example, the storage elements may take the form of solid-state memory such as, for example, 2D NAND, 3D NAND memory, multi-level cell memory, triple level cell memory, quad-level cell memory, penta-level cell memory or any combination thereof.

The controller 650 may include circuitry for executing instructions. The instructions may originate from firmware 660 associated with the data storage device 610. In another example, the instructions may originate from the host device 605. Accordingly, the controller 650 may include circuitry such as one or more processors, a microcontroller, a DSP, an ASIC, an FPGA, hard-wired logic, analog circuitry and/or a combination thereof. In another example, the controller 650 may include a SoC.

The data storage device 610 may also include secondary memory 675. The secondary memory 675 may be a rotating magnetic disk or non-volatile solid-state memory, such as flash memory. While the description herein refers to solid-state memory generally, it is understood that solid-state memory may comprise one or more of various types of memory devices such as flash integrated circuits, NAND memory (e.g., single-level cell (SLC) memory, multi-level cell (MLC) memory (i.e., two or more levels), or any combination thereof), NOR memory, EEPROM, other discrete Non-Volatile Memory (NVM) chips, or any combination thereof.

In some examples, the memory device 655 is capable of storing data at a byte-addressable level, as opposed to other types of non-volatile memory that have a smallest writable data size such as a page size of 4 KB or a sector size of 512 Bytes.

In some examples, the memory device 655 may also store a mapping table 665 and/or an address space 670. In some examples, the controller 650 can associate portions of data stored in the secondary memory 675 with unique identifiers. The unique identifiers may be stored in the memory device 655 and be used by the operating system 625 to access stored data. For example, the mapping table 665 can provide a mapping of unique identifiers with indications of physical locations (e.g., Physical Block Addresses (PBAs)) where the corresponding portions of data are stored in the memory device 655 and/or the secondary memory 675.

In some examples, the firmware 660 may store, maintain, be associated with or otherwise have access to a mapping table (e.g., mapping table 665) that stores and/or maintains mapping information for the various DNA sequences such as described above.

As briefly discussed above, the memory device 655 may also include address space 670. The address space 670 can serve as at least a portion of an address space used by the processor 615. In an example, the address space 670 can store data at a byte-addressable level that can be accessed by the processor 615 (e.g., via the communication interface 640).

For example, the data storage device 610 may provide the host device 605 with an indication of the address space 670. The host device 605 may then associate an address range for the address space 670 and an indication that this address range is to be used as a byte-addressable address space, such as for a page cache.

In another example, the host device 605 may manage the data storage device 610 such that the processor 615 can directly access address space 670. For example, the data storage device 610 may provide logical to physical address translation information to the host device 605, which can be called by the host device 605 and executed by the processor 615 and/or the controller 650. In some examples, the controller 650 may include or otherwise be associated with a flash translation layer (FTL). The FTL may map the logical block addresses to the physical addresses of the memory device 655.

Although FIG. 6 illustrates the host device 605 being separate from the data storage device 510, the host device 605 and the data storage device 610, as well the various components described, may be part of a single device or part of multiple devices.

In accordance with the above, examples of the present disclosure describe a computing system, comprising: a memory device storing an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defines a string of data representing a sequence of one or more deoxyribonucleic acid (DNA) nucleotide bases; and at least one processor executing instructions that are configured to cause the at least one processor to: identify an input string of input data; segment the input string into a plurality of input tuples, each input tuple of the plurality of input tuples being k bits in size; for each input tuple of the plurality of input tuples, generate a plurality of encoded tuples by: identifying an entry of the encoding table that has an input segment equal to the input tuple; and adding, to the plurality of encoded tuples, an encoded tuple that includes an encoded segment in the identified entry of the encoding table; convert the plurality of encoded tuples into a DNA sequence string of DNA nucleotides by concatenating the plurality of encoded tuples in an order defined by the plurality of input tuples; and cause at least one DNA molecule to be synthesized using the DNA sequence string of DNA nucleotides. In an example, the string of data defined by each encoded segment of the plurality of encoded segments is comprised of one or more data elements, each data element representing one of four DNA nucleotide bases. In an example, the instructions further cause the at least one processor to dynamically create the encoding table based at least in part on a first size parameter, k, a second size parameter, n, and one or more exclusion conditions, wherein dynamically creating the encoding table comprises: creating a first column associated with input segments, the first column being configured of at least size k bits; creating a second column associated with encrypted segments, the second column being configured of at least size n bits; creating one row in the encoding table for each unique encrypted segment in a domain of the encrypted segments, the second column of each row being populated with the associated unique encrypted segment; identifying a subset of rows of the encoding table based, at least in part, on whether the encrypted segment matches one or more of the exclusion conditions; and populating each row of the identified subset of rows with a unique input segment. In an example, identifying the subset of rows of the encoding table further comprises: determining that a first row matches at least one of the exclusion conditions based, at least in part, on comparing an encoded segment of the first row to a pattern associated with at least one of the exclusion conditions; and excluding the first row from the identified subset of rows based on the determining. In an example, the pattern is provided in regular expression (regex) syntax. In an example, the pattern associated with the at least one of the exclusion condition includes one of: (i) a pattern configured to identify encoded segments that have at least two repeating, adjacent base pairs; and (ii) a pattern configured to identify encoded segments based on T-base content. In an example, the instructions further cause the at least one processor to: receive a sequence string generated from a sequencing of the at least one DNA molecule; decode the sequence string using the encoding table; and generate an output string of output data based on the decoding.

Examples of the present disclosure also describe a computer-implemented method comprising: receiving an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defines a string of data representing a sequence of one or more deoxyribonucleic acid (DNA) nucleotide bases; identifying an input string of input data; segmenting the input string into a plurality of input tuples, each input tuple of the plurality of input tuples being k bits in size; for each input tuple of the plurality of input tuples, generate a plurality of encoded tuples by: identifying an entry of the encoding table that has an input segment equal to the input tuple; and adding, to the plurality of encoded tuples, an encoded tuple that includes an encoded segment in the identified entry of the encoding table; converting the plurality of encoded tuples into a DNA sequence string of DNA nucleotides by concatenating the plurality of encoded tuples in an order defined by the plurality of input tuples; and transmitting the DNA sequence string of DNA nucleotides to be used for synthesizing at least one DNA molecule. In an example, the string of data defined by each encoded segment of the plurality of encoded segments is comprised of one or more data elements, each data element representing one of four DNA nucleotide bases. In an example, the method further comprises automatically creating, by at least one processor, the encoding table based at least in part on a first size parameter, k, a second size parameter, n, and one or more exclusion conditions, wherein dynamically creating the encoding table comprises: creating a first column associated with input segments, the first column being configured of at least size k bits; creating a second column associated with encrypted segments, the second column being configured of at least size n bits; creating one row in the encoding table for each unique encrypted segment in a domain of the encrypted segments, the second column of each row being populated with the associated unique encrypted segment; identifying a subset of rows of the encoding table based, at least in part, on whether the encrypted segment matches one or more of the exclusion conditions; and populating each row of the identified subset of rows with a unique input segment. In an example, identifying the subset of rows of the encoding table further comprises: determining that a first row matches at least one of the exclusion conditions based, at least in part, on comparing an encoded segment of the first row to a pattern associated with at least one of the exclusion conditions; and excluding the first row from the identified subset of rows based on the determining. In an example, the pattern is provided in regular expression (regex) syntax. In an example, the pattern associated with the at least one of the exclusion condition includes one of: (i) a pattern configured to identify encoded segments that have at least two repeating, adjacent base pairs; and (ii) a pattern configured to identify encoded segments based on T-base content. In an example, the method further comprises receiving a sequence string generated from a sequencing of the at least one DNA molecule; decoding the sequence string using the encoding table; and generating an output string of output data based on the decoding.

Examples of the present disclosure also describe a non-transitory, computer-readable storage medium comprising instruction that, when executed by at least one processor, causes the at least one processor to: identify an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defines a string of data representing a sequence of one or more deoxyribonucleic acid (DNA) nucleotide bases; identify an input string of input data; means for segmenting the input string into a plurality of input tuples, each input tuple of the plurality of input tuples being k bits in size; for each input tuple of the plurality of input tuples, generate a plurality of encoded tuples by: means for identifying an entry of the encoding table that has an input segment equal to the input tuple; and means for adding, to the plurality of encoded tuples, an encoded tuple that includes an encoded segment in the identified entry of the encoding table; means for converting the plurality of encoded tuples into a DNA sequence string of DNA nucleotides by concatenating the plurality of encoded tuples in an order defined by the plurality of input tuples; and transmit the DNA sequence string of DNA nucleotides to be used for synthesizing at least one DNA molecule. In an example, the string of data defined by each encoded segment of the plurality of encoded segments is comprised of one or more data elements, each data element representing one of four DNA nucleotide bases. In an example, the non-transitory, computer-readable storage medium further comprises means for creating, by at least one processor, the encoding table based at least in part on a first size parameter, k, a second size parameter, n, and one or more exclusion conditions, wherein dynamically creating the encoding table comprises: means for creating a first column associated with input segments, the first column being configured of at least size k bits; means for creating a second column associated with encrypted segments, the second column being configured of at least size n bits; means for creating one row in the encoding table for each unique encrypted segment in a domain of the encrypted segments, the second column of each row being populated with the associated unique encrypted segment; means for identifying a subset of rows of the encoding table based, at least in part, on whether the encrypted segment matches one or more of the exclusion conditions; and means for populating each row of the identified subset of rows with a unique input segment. In an example, identifying the subset of rows of the encoding table further comprises: means for determining that a first row matches at least one of the exclusion conditions based, at least in part, on comparing an encoded segment of the first row to a pattern associated with at least one of the exclusion conditions; and means for excluding the first row from the identified subset of rows based on the determining. In an example, the pattern is provided in regular expression (regex) syntax. In an example, the pattern associated with the at least one of the exclusion condition includes one of: (i) a pattern configured to identify encoded segments that have at least two repeating, adjacent base pairs; and (ii) a pattern configured to identify encoded segments based on T-base content.

The term computer-readable media as used herein may include computer storage media. Computer storage media may include volatile and nonvolatile, removable and non-removable media implemented in any method or technology for storage of information, such as computer readable instructions, data structures, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by a computing device. Any such computer storage media may be part of the computing device. Computer storage media does not include a carrier wave or other propagated or modulated data signal.

Additionally, examples described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various examples.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The description and illustration of one or more aspects provided in the present disclosure are not intended to limit or restrict the scope of the disclosure in any way. The aspects, examples, and details provided in this disclosure are considered sufficient to convey possession and enable others to make and use the best mode of claimed disclosure.

The claimed disclosure should not be construed as being limited to any aspect, example, or detail provided in this disclosure. Regardless of whether shown and described in combination or separately, the various features (both structural and methodological) are intended to be selectively rearranged, included or omitted to produce an example with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

Aspects of the present disclosure have been described above with reference to schematic flowchart diagrams and/or schematic block diagrams of methods, apparatuses, systems, and computer program products according to examples of the disclosure. It will be understood that each block of the schematic flowchart diagrams and/or schematic block diagrams, and combinations of blocks in the schematic flowchart diagrams and/or schematic block diagrams, can be implemented by computer program instructions. These computer program instructions may be provided to a processor of a computer or other programmable data processing apparatus to produce a machine, such that the instructions, which execute by way of the processor or other programmable data processing apparatus, create means for implementing the functions and/or acts specified in the schematic flowchart diagrams and/or schematic block diagrams block or blocks.

References to an element herein using a designation such as "first," "second," and so forth does not generally limit the quantity or order of those elements. Rather, these designations may be used as a method of distinguishing between two or more elements or instances of an element. Thus, reference to first and second elements does not mean that only two elements may be used or that the first element precedes the second element. Additionally, unless otherwise stated, a set of elements may include one or more elements.

Terminology in the form of "at least one of A, B, or C" or "A, B, C, or any combination thereof" used in the description or the claims means "A or B or C or any combination of these elements." For example, this terminology may include A, or B, or C, or A and B, or A and C, or A and B and C, or 2A, or 2B, or 2C, or 2A and B, and so on. As an additional example, "at least one of: A, B, or C" is intended to cover A, B, C, A-B, A-C, B-C, and A-B-C, as well as multiples of the same members. Likewise, "at least one of: A, B, and C" is intended to cover A, B, C, A-B, A-C, B-C, and A-B-C, as well as multiples of the same members.

Similarly, as used herein, a phrase referring to a list of items linked with "and/or" refers to any combination of the items. As an example, "A and/or B" is intended to cover A alone, B alone, or A and B together. As another example, "A, B and/or C" is intended to cover A alone, B alone, C alone, A and B together, A and C together, B and C together, or A, B, and C together.

What is claimed is:

1. A computing system, comprising:

a memory device configured to store an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defining a string of data representing a sequence of one or more deoxyribonucleic acid (DNA) nucleotide bases; and at least one processor configured to execute instructions that are configured to cause the at least one processor, individually or in combination, to:

identify an input string of input data;

segment the input string into a plurality of input tuples, each input tuple of the plurality of input tuples being k bits in size;

for each input tuple of the plurality of input tuples, generate a plurality of encoded tuples by:

identifying an entry of the encoding table that has an input segment equal to the input tuple; and adding, to the plurality of encoded tuples, an encoded tuple that includes an encoded segment in the identified entry of the encoding table;

convert the plurality of encoded tuples into a DNA sequence string of DNA nucleotides by concatenating the plurality of encoded tuples in an order defined by the plurality of input tuples; and cause at least one DNA molecule to be synthesized using the DNA sequence string of DNA nucleotides.

2. The computing system of claim 1, wherein the string of data defined by each encoded segment of the plurality of encoded segments is comprised of one or more data elements, each data element representing one of four DNA nucleotide bases.

3. The computing system of claim 1, wherein the instructions further cause the at least one processor, individually or in combination, to dynamically create the encoding table based at least in part on a first size parameter, k, a second size parameter, n, and one or more exclusion conditions, wherein dynamically creating the encoding table comprises:

creating a first column associated with input segments, the first column being configured of at least size k bits;

creating a second column associated with encrypted segments, the second column being configured of at least size n bits;

creating one row in the encoding table for each unique encrypted segment in a domain of the encrypted segments, the second column of each row being populated with the associated unique encrypted segment;

identifying a subset of rows of the encoding table based, at least in part, on whether the encrypted segment matches one or more of the exclusion conditions; and populating each row of the identified subset of rows with a unique input segment.

4. The computing system of claim 3, wherein identifying the subset of rows of the encoding table further comprises:

determining that a first row matches at least one of the exclusion conditions based, at least in part, on comparing an encoded segment of the first row to a pattern associated with at least one of the exclusion conditions; and excluding the first row from the identified subset of rows based on the determining.

5. The computing system of claim 4, wherein the pattern is provided in regular expression (regex) syntax.

6. The computing system of claim 4, wherein the pattern includes one of: (i) a pattern configured to identify encoded segments that have at least two repeating, adjacent base pairs; and (ii) a pattern configured to identify encoded segments based on T-base content.

7. The computing system of claim 1, wherein the instructions further cause the at least one processor, individually or in combination, to:

receive a sequence string generated from a sequencing of the at least one DNA molecule;

decode the sequence string using the encoding table; and generate an output string of output data based on the decoding.

8. A computer-implemented method comprising:

receiving an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defining a string of data representing a sequence of one or more deoxyribonucleic acid (DNA) nucleotide bases;

identifying an input string of input data;

segmenting the input string into a plurality of input tuples, each input tuple of the plurality of input tuples being k bits in size;

for each input tuple of the plurality of input tuples, generating a plurality of encoded tuples by:

identifying an entry of the encoding table that has an input segment equal to the input tuple; and adding, to the plurality of encoded tuples, an encoded tuple that includes an encoded segment in the identified entry of the encoding table;

converting the plurality of encoded tuples into a DNA sequence string of DNA nucleotides by concatenating the plurality of encoded tuples in an order defined by the plurality of input tuples; and transmitting the DNA sequence string of DNA nucleotides to be used for synthesizing at least one DNA molecule.

9. The method of claim 8, wherein the string of data defined by each encoded segment of the plurality of encoded segments is comprised of one or more data elements, each data element representing one of four DNA nucleotide bases.

10. The method of claim 8, further comprising automatically creating, by at least one processor, individually or in combination, the encoding table based at least in part on a first size parameter, k, a second size parameter, n, and one or more exclusion conditions, wherein automatically creating the encoding table comprises:

creating a first column associated with input segments, the first column being configured of at least size k bits;

creating a second column associated with encrypted segments, the second column being configured of at least size n bits;

creating one row in the encoding table for each unique encrypted segment in a domain of the encrypted segments, the second column of each row being populated with the associated unique encrypted segment;

identifying a subset of rows of the encoding table based, at least in part, on whether the encrypted segment matches one or more of the exclusion conditions; and populating each row of the identified subset of rows with a unique input segment.

11. The method of claim 10, wherein identifying the subset of rows of the encoding table further comprises:

determining that a first row matches at least one of the exclusion conditions based, at least in part, on comparing an encoded segment of the first row to a pattern associated with at least one of the exclusion conditions; and excluding the first row from the identified subset of rows based on the determining.

12. The method of claim 11, wherein the pattern is provided in regular expression (regex) syntax.

13. The method of claim 11, wherein the pattern includes one of: (i) a pattern configured to identify encoded segments that have at least two repeating, adjacent base pairs; and (ii) a pattern configured to identify encoded segments based on T-base content.

14. The method of claim 8, further comprising:

receiving a sequence string generated from a sequencing of the at least one DNA molecule;

decoding the sequence string using the encoding table; and generating an output string of output data based on the decoding.

15. A non-transitory, computer-readable storage medium comprising instructions that, when executed by at least one processor, cause the at least one processor, individually or in combination, to:

identify an encoding table, the encoding table defining a plurality of mappings between a plurality of input segments and a plurality of encoded segments, each input segment of the plurality of input segments being associated in the encoding table with an encoded segment of the plurality of encoded segments, each encoded segment defining a string of data representing a sequence of one or more deoxyribonucleic acid (DNA) nucleotide bases;

identify an input string of input data;

segment the input string into a plurality of input tuples, each input tuple of the plurality of input tuples being k bits in size;

for each input tuple of the plurality of input tuples, generate a plurality of encoded tuples by:

identifying an entry of the encoding table that has an input segment equal to the input tuple; and adding, to the plurality of encoded tuples, an encoded tuple that includes an encoded segment in the identified entry of the encoding table;

convert the plurality of encoded tuples into a DNA sequence string of DNA nucleotides by concatenating the plurality of encoded tuples in an order defined by the plurality of input tuples; and transmit the DNA sequence string of DNA nucleotides to be used for synthesizing at least one DNA molecule.

16. The non-transitory, computer-readable storage medium of claim 15, wherein the string of data defined by each encoded segment of the plurality of encoded segments is comprised of one or more data elements, each data element representing one of four DNA nucleotide bases.

17. The non-transitory, computer-readable storage medium of claim 15, further comprising instructions that, when executed by the at least one processor, cause the at least one processor, individually or in combination, to create the encoding table based at least in part on a first size parameter, k, a second size parameter, n, and one or more exclusion conditions, wherein creating the encoding table comprises:

creating a first column associated with input segments, the first column being configured of at least size k bits;

creating a second column associated with encrypted segments, the second column being configured of at least size n bits;

creating one row in the encoding table for each unique encrypted segment in a domain of the encrypted segments, the second column of each row being populated with the associated unique encrypted segment;

identifying a subset of rows of the encoding table based, at least in part, on whether the encrypted segment matches one or more of the exclusion conditions; and populating each row of the identified subset of rows with a unique input segment.

18. The non-transitory, computer-readable storage medium of claim 17, wherein identifying the subset of rows of the encoding table further comprises:

determining that a first row matches at least one of the exclusion conditions based, at least in part, on comparing an encoded segment of the first row to a pattern associated with at least one of the exclusion conditions; and excluding the first row from the identified subset of rows based on the determining.

19. The non-transitory, computer-readable storage medium of claim 18, wherein the pattern is provided in regular expression (regex) syntax.

20. The non-transitory, computer-readable storage medium of claim 18, wherein the pattern includes one of: (i) a pattern configured to identify encoded segments that have at least two repeating, adjacent base pairs; and (ii) a pattern configured to identify encoded segments based on T-base content.

* * * * *